(12) United States Patent
Stössel et al.

(10) Patent No.: US 7,825,249 B2
(45) Date of Patent: *Nov. 2, 2010

(54) METAL COMPLEXES

(75) Inventors: Philipp Stössel, Frankfurt (DE); Esther Breuning, Niedernhausen (DE)

(73) Assignee: Merck Patent GmbH, Darmstadt (DE)

( * ) Notice: Subject to any disclaimer, the term of this patent is extended or adjusted under 35 U.S.C. 154(b) by 1006 days.

This patent is subject to a terminal disclaimer.

(21) Appl. No.: 11/596,733

(22) PCT Filed: May 14, 2005

(86) PCT No.: PCT/EP2005/005309

§ 371 (c)(1),
(2), (4) Date: Nov. 17, 2006

(87) PCT Pub. No.: WO2005/113563

PCT Pub. Date: Dec. 1, 2005

(65) Prior Publication Data

US 2007/0249834 A1 Oct. 25, 2007

(30) Foreign Application Priority Data

May 19, 2004 (DE) ............ 10 2004 024 736

(51) Int. Cl.
C07F 15/00 (2006.01)
H01L 51/40 (2006.01)

(52) U.S. Cl. ............ 546/6; 556/7; 556/9; 556/27; 556/136; 556/137; 548/101; 548/110; 548/402; 548/405; 546/2; 546/4; 546/13; 438/99; 257/40

(58) Field of Classification Search ............ 546/2, 546/4, 6, 13; 548/101, 110, 402, 405; 556/7, 556/9, 27, 136, 137; 438/99; 257/40
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,621,131 A | 4/1997 | Kreuder et al. | |
| 5,679,760 A | 10/1997 | Mullen et al. | |
| 6,653,438 B1 | 11/2003 | Spreitzer et al. | |
| 6,753,156 B1 | 6/2004 | Mathis et al. | |
| 7,084,273 B2 | 8/2006 | Stössel et al. | |
| 2006/0142552 A1 | 6/2006 | Bach et al. | |
| 2006/0142604 A1 | 6/2006 | Bach et al. | |
| 2006/0149022 A1 | 7/2006 | Parham et al. | |
| 2006/0220004 A1 | 10/2006 | Stossel et al. | |
| 2008/0027220 A1* | 1/2008 | Stossel et al. | 544/225 |

FOREIGN PATENT DOCUMENTS

| | | |
|---|---|---|
| DE | 10 2004 020 298 | 11/2005 |
| DE | 10 2004 023 278 | 12/2005 |
| EP | 0 707 020 | 4/1996 |
| EP | 0 842 208 | 5/1998 |
| EP | 0 894 107 | 2/1999 |
| EP | 1 028 136 | 8/2000 |
| WO | WO-92/18552 | 10/1992 |
| WO | WO97/05184 | 2/1997 |
| WO | WO-99/15896 | 4/1999 |
| WO | WO-00/22026 | 4/2000 |
| WO | WO-02/060910 | 8/2002 |
| WO | WO-2004/070772 | 8/2004 |
| WO | WO-2004/081017 | 9/2004 |
| WO | WO-2004/085449 | 10/2004 |
| WO | WO-2004/108738 | 12/2004 |
| WO | WO-2004/113468 | 12/2004 |
| WO | WO-2005/014689 | 2/2005 |

OTHER PUBLICATIONS

Database Chemidplus Online, National Library of Medicine, Accession No. RN: 12678-01-02, Sep. 9, 2004.
Lehn, J.-M. et al., "Synthesis of Macrobicyclic Cryptates Incorporating Bithiazole, Bisimidazole and Bipyrimidine Binding Subunits", Tetrahedron Letters, vol. 30, No. 17 (1989), pp. 2209-2212.
Römpp Chemistry Dictionary, "1,10- Phenanthrolin", 9th Edition , 1992.

* cited by examiner

*Primary Examiner*—Porfirio Nazario Gonzalez
(74) *Attorney, Agent, or Firm*—Connolly Bove Lodge & Hutz LLP

(57) ABSTRACT

The invention relates to novel metal complexes. Said compounds can be used as functional material in a series of different applications which in the broadest sense can be attributed to the electronics industry. The inventive compounds are described by the formula (1) and by compounds (1) to (52).

26 Claims, No Drawings

METAL COMPLEXES

RELATED APPLICATIONS

This application is national stage application (under 35 U.S.C. 371) of PCT/EP2005/005309 filed May 14, 2005, which claims benefit of German application 10 2004 024 736.6 filed May 19, 2004.

Organometallic compounds, especially compounds of the $d^8$ metals, will in the near future be used as functional materials in a number of applications of different types which can be ascribed to the electronics industry in the broadest sense. In the case of organic electroluminescent devices or organic light-emitting diodes (OLEDs) based on organic components (for example U.S. Pat. No. 4,539,507, U.S. Pat. No. 5,151,629), the market introduction has already taken place, as confirmed by the car radios from Pioneer and the mobile telephones with an "organic display" from Pioneer and SNMD. Other products of this type are just about to be introduced. Significant improvements are nevertheless still necessary here in order to make these displays a true competitor to the liquid-crystal displays (LCDs) which currently dominate the market.

A development which has been evident in recent years is the use of organometallic complexes which exhibit phosphorescence instead of fluorescence (M. A. Baldo et al., *Appl. Phys. Lett.* 1999, 75, 4-6). For theoretical spin-statistical reasons, an up to four-fold energy and power efficiency is possible using organometallic compounds as phosphorescence emitters. Whether this development will succeed depends on whether corresponding device compositions are found which are also able to implement these advantages (triplet emission=phosphorescence compared with singlet emission=fluorescence) in OLEDs. Essential conditions which may be mentioned here are, in particular, a long operating lifetime and high thermal stability, both during operation and also during vapour deposition. This is of particular interest, against the background of the rareness of the metals, in the case of ruthenium, osmium, rhodium, iridium, gold and platinum compounds in order to enable resource-conserving use thereof.

Phosphorescent OLEDs to date exhibit the following weak points, inter alia:
1. The operating lifetime is in many cases still clearly too short, which is preventing the market introduction of (phosphorescent) OLEDs.
2. Many of the known metal complexes have low thermal stability. During vacuum deposition of the metal complexes, this inevitably always results in liberation of organic pyrolysis products, which in some cases, even in small amounts, considerably shorten the operating lifetime of the OLEDs. In particular, however, also during purification of the metal complexes by sublimation and during vapour deposition by vacuum processes, it would be desirable to have available significantly more temperature-stable complexes since decomposition results in large losses of the complexes.
3. Many complexes which are to be employed as phosphorescence emitters, in particular red-emitting complexes, are highly oxidation-sensitive. This makes handling considerably more difficult since both the synthesis and also the purification and all further processing steps during device production have to be carried out with strict exclusion of oxygen. It would be desirable here to have available less sensitive complexes.
4. Many of the metal complexes mentioned in the literature which have hitherto been used in OLEDs are homoleptic, (pseudo)octahedral complexes consisting of a central metal coordinated to three bidentate ligands. Complexes of this structural type can occur in two isomeric forms, the meridional and the facial isomers. One of the two isomers is frequently only slightly preferred thermo-dynamically. dynamically. This results in one or other of the isomers or even mixtures being formed under certain conditions, for example a certain sublimation temperature. This is undesired since the two isomers frequently differ significantly in their physical properties (emission spectrum, charge-transport properties, etc.), and the properties of an OLED may thus differ significantly from one another even in the case of slight changes to the production process.

There was therefore a demand for alternative compounds which do not have the above-mentioned weak points, but are at least equivalent to the known metal complexes in respect of efficiency and emission colour.

Surprisingly, it has now been found that cryptates have excellent properties surpassing the prior art on use in organic electronic components, in particular as triplet emitters. This applies, in particular, to the thermal stability and the lifetime. The present invention relates to these compounds. The class of organometallic cryptates described below in greater detail and the use thereof in electro-optical components is novel, but their efficient preparation and availability as pure substances is of major importance for this purpose.

The invention relates to organometallic cryptates of the formula (1)

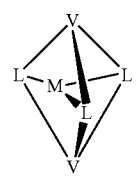

Formula (1)

containing at least one metal M coordinated to a cryptand K of the formula (2)

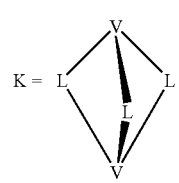

Formula (2)

where V is a bridging unit, identically or differently on each occurrence, containing 1 to 80 atoms which covalently bonds the three part-ligands L, which may be identical or different on each occurrence, to one another; the three part-ligands L are described by formula (3)

Formula (3)

where DCy is a substituted or unsubstituted cyclic group which contains at least one donor atom in the ring or exocyclically bonded, via which atom the cyclic group DCy is bonded to the metal, and CCy is a substituted or unsubstituted cyclic group which contains at least one carbon atom, via which the cyclic group CCy is bonded to the metal; the groups DCy and CCy are bonded to one another via a covalent bond and may additionally be linked to one another via substituents and thus define a polycyclic, aliphatic or aromatic ring system.

For the purposes of this invention, an organometallic compound is taken to mean a compound which has at least one direct metal-carbon bond.

For the purposes of this invention, a cryptate is taken to mean a compound between a cryptand and a metal ion in which the metal ion is surrounded in a three-dimensional manner by the bridges of the complex-forming cryptand.

For the purposes of this invention, a cryptand is intended to be taken to mean a macropolycyclic ligand, in particular a ligand in which two bridgehead atoms or bridgehead groups are connected by three bridges, each of which is capable of coordinating to a metal atom or ion.

The cyclic groups DCy and CCy, which may be heterocycles or in the case of CCy also homocycles, may be saturated, unsaturated or aromatic. The groups are preferably aromatic.

Preference is given to compounds of the formula (1) according to the invention, characterised in that they are not charged, i.e. are electrically neutral.

Preference is given to compounds of the formula (1) according to the invention, characterised in that at least one of the part-ligands L, preferably at least two of the part-ligands L and particularly preferably all three part-ligands L, are singly negatively charged.

Preference is given to compounds of the formula (1) according to the invention, characterised in that all part-ligands L within a cryptand K are identical.

Preference is likewise given to compounds of the formula (1) according to the invention, characterised in that at least two part-ligands L are different from one another.

Preference is given to compounds of the formula (1) according to the invention, characterised in that the bridging unit V contains, as linking atom, an element from main group 3, 4, 5 or 6 or a 3- to 6-membered homo- or heterocycle.

The bridging unit V may be neutral, singly negatively charged or singly positively charged. The charge of V is preferably selected here in such a way that a neutral complex is formed. Thus, for example, two neutral bridging units V are preferred in the case of a trivalent metal ion $M^{3+}$ and three singly negative part-ligands L. Preference is furthermore given to a neutral and a singly negative bridging unit V in the case of a tetravalent metal ion $M^{4+}$ and three singly negative part-ligands L. Preference is furthermore given to two singly negative bridging units V in the case of a pentavalent metal ion $M^{5+}$ and three singly negative part-ligands L. Preference is furthermore given to a neutral and a singly positive bridging unit V in the case of a divalent metal ion $M^{2+}$ and three singly negative part-ligands L. Preference is furthermore given to two singly positive bridging units V in the case of a monovalent metal ion $M^+$ and three singly negative part-ligands L.

Preference is given to compounds of the formula (1) according to the invention, characterised in that the cryptand K of the formula (4) produces a facial coordination at the metal M:

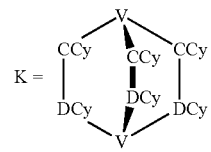

Formula (4)

Preference is likewise given to compounds of the formula (1) according to the invention, characterised in that the cryptand K of the formula (5) produces a meridional coordination at the metal M:

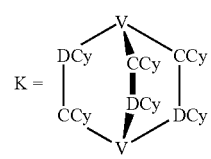

Formula (5)

For the purposes of this application, facial or meridional coordination describes the environment of the metal M with the six donor atoms. Facial coordination is present if three identical donor atoms occupy a triangular face in the (pseudo) octahedral coordination polyhedron and three donor atoms which are identical, but are different from the first donor atoms, occupy another triangular face in the (pseudo)octahedral coordination polyhedron. In the case of meridional coordination, three identical donor atoms occupy the first meridian in the (pseudo)octahedral coordination polyhedron and three donor atoms which are identical, but are different from the first donor atoms, occupy the other meridian in the (pseudo)octahedral coordination polyhedron. This is shown below with reference to the example of coordination of three N donor atoms and three C donor atoms (scheme 1). Since this description relates to donor atoms and not to the rings CCy and DCy which provide these donor atoms, the three rings CCy and the three rings DCy may be identical or different on each occurrence and nevertheless correspond to facial or meridional coordination for the purposes of this application. Identical donor atoms are taken to mean those which consist of the same elements (for example nitrogen), irrespective of whether these elements are incorporated into different, optionally cyclic structures.

Scheme 1:

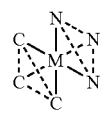 

facial coordination    meridional coordination

Preference is given to organometallic cryptates as described by compounds (1) to (4) with facial coordination geometry at the metal Compound (1)

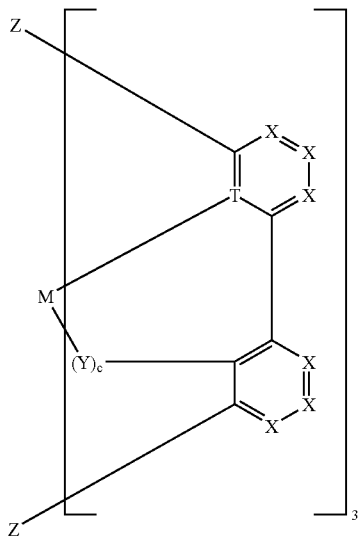

Compound (2)

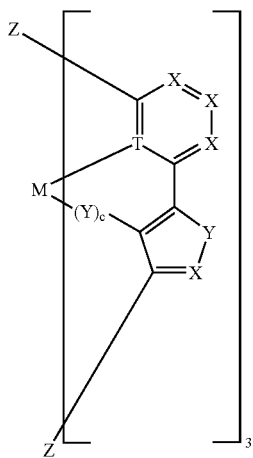

Compound (3)

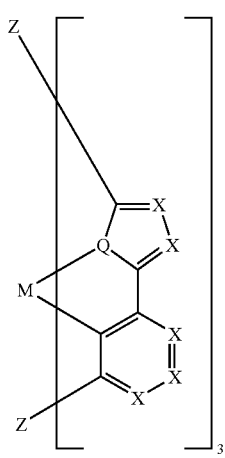

Compound (4)

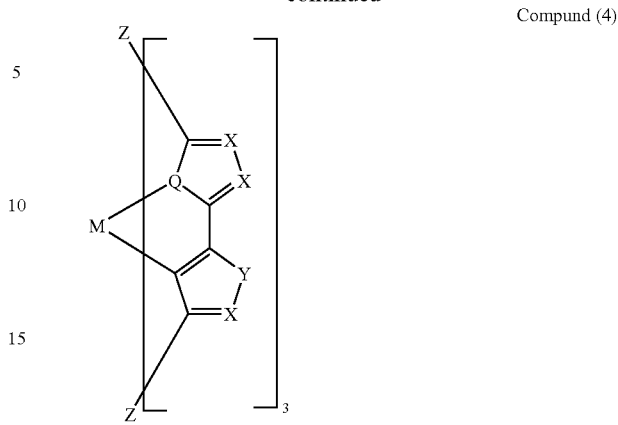

where the symbols and indices have the following meaning:

M is on each occurrence, identically or differently, a main-group metal ion, a transition-metal ion or a lanthanoid ion;

Q is, identically or differently on each occurrence, O, S, Se, Te or N;

T is, identically or differently on each occurrence, N, P or C;

X is, identically or differently on each occurrence, CR, N or P;

Y is, identically or differently on each occurrence, $NR^1$, O, S, Se, Te, SO, SeO, TeO, $SO_2$, $SeO_2$, $TeO_2$, $R^1PO$;

Z is, identically or differently on each occurrence, B, $BR^-$, $B(CR_2)_3$, $RB(CR_2)_3^-$, $B(O)_3$, $RB(O)_3^-$, $B(CR_2CR_2)_3$, $RB(CR_2CR_2)_3^-$, $B(CR_2O)_3$, $RB(CR_2O)_3^-$, $B(OCR_2)_3$, $RB(OCR_2)_3^-$, $Al(O)_3$, $RAl(O)_3^-$, $Al(OCR_2)_3$, $RAl(OCR_2)_3^-$, CR, $CO^-$, $CNR^1_2$, $RC(CR_2)_3$, $RC(O)_3$, $RC(CR_2CR_2)_3$, $RC(CR_2O)_3$, $RC(OCR_2)_3$, $RC(SiR_2)_3$, $RC(SiR_2CR_2)_3$, $RC(CR_2SiR_2)_3$, $RC(SiR_2SiR_2)_3$, cis,cis-1,3,5-$(CR_2)_3C_6H_3$, 1,3,5-$(CR_2)_3C_6H_3$, SiR, $RSi(CR_2)_3$, $RSi(O)_3$, $RSi(CR_2CR_2)_3$, $RSi(OCR_2)_3$, $RSi(CR_2O)_3$, $RSi(SiR_2)_3$, $RSi(SiR_2CR_2)_3$, $RSi(CR_2SiR_2)_3$, $RSi(SiR_2SiR_2)_3$, N, NO, $NR^+$, $N(CR_2)_3$, $RN(CR_2)_3^+$, $N(C=O)_3$, $N(CR_2CR_2)_3$, $RN(CR_2CR_2)^+$, P, PO, PS, PSe, PTe, $P(O)_3$, $PO(O)_3$, $P(OCR_2)_3$, $PO(OCR_2)_3$, $P(CR_2)_3$, $PO(CR_2)_3$, $P(CR_2CR_2)_3$, $PO(CR_2CR_2)_3$, As, AsO, AsS, AsSe, AsTe, $As(O)_3$, $AsO(O)_3$, $As(OCR_2)_3$, $AsO(OCR_2)_3$, $As(CR_2)_3$, $AsO(CR_2)_3$, $As(CR_2CR_2)_3$, $AsO(CR_2CR_2)_3$, Sb, SbO, SbS, SbSe, SbTe, $Sb(O)_3$, $SbO(O)_3$, $Sb(OCR_2)_3$, $SbO(OCR_2)_3$, $Sb(CR_2)_3$, $SbO(CR_2)_3$, $Sb(CR_2CR_2)_3$, $SbO(CR_2CR_2)_3$, Bi, BiO, BiS, BiSe, BiTe, $Bi(O)_3$, $BiO(O)_3$, $Bi(OCR_2)_3$, $BiO(OCR_2)_3$, $Bi(CR_2)_3$, $BiO(CR_2)_3$, $Bi(CR_2CR_2)_3$, $BiO(CR_2CR_2)_3$, $S^+$, $S(CR_2)_3^+$, $S(CR_2CR_2)_3^+$, $Se^+$, $Se(CR_2)_3^+$, $Se(CR_2CR_2)_3^+$, $Te^+$, $Te(CR_2)_3^+$, $Te(CR_2CR_2)_3^+$;

R is, identically or differently on each occurrence, H, F, Cl, Br, I, OH, $NO_2$, CN, a straight-chain, branched or cyclic alkyl or alkoxy group having 1 to 20 C atoms, in which one or more non-adjacent $CH_2$ groups may be replaced by $-R^1C=CR^1-$, $-C\equiv C-$, $Si(R^1)_2$, $Ge(R^1)_2$, $Sn(R^1)_2$, C=O, C=S, C=Se, $C=NR^1$, $-O-$, $-S-$, $-NR^1-$ or $-CONR^1-$ and in which one or more H atoms may be replaced by F, or an aromatic or heteroaromatic ring system having 1 to 14 C atoms, which may be substituted by one or more non-aromatic radicals R, where two or more substituents R, both on the same ring and also on the two different rings, together may in turn define a further mono- or polycyclic, aliphatic or aromatic and/or benzo-fused ring system;

$R^1$ is, identically or differently on each occurrence, H or an aliphatic or aromatic hydrocarbon radical having 1 to 20 C atoms;

c is, identically or differently on each occurrence, 0 or 1, with the proviso that c=0 if the symbol T in the corresponding part-ligand stands for N or P.

In addition, preference is likewise given to compounds (5) to (8) with meridional coordination geometry at the metal Compound (5)

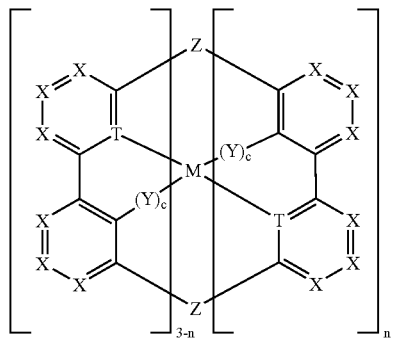

Compound (6)

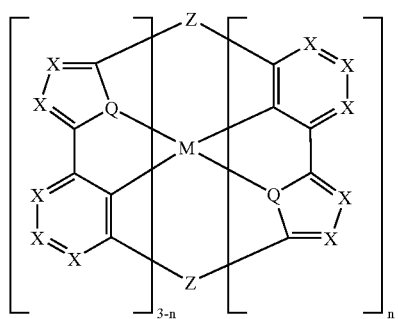

Compound (7)

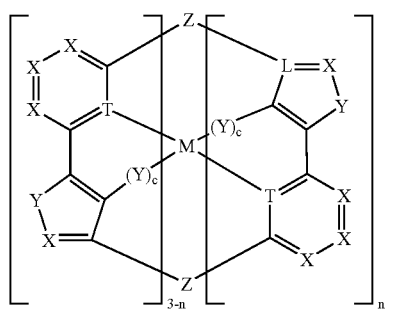

Compound (8)

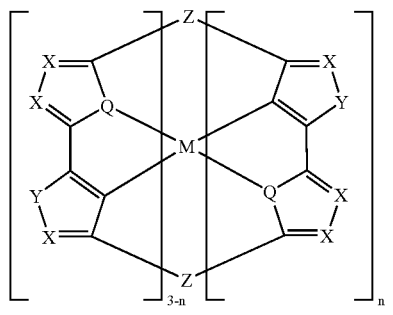

where the symbols and indices M, Q, T, X, Y, Z, R, $R^1$ and c have the meanings indicated above, and n is equal to 1 or 2.

The invention furthermore relates to compounds which simultaneously contain different part-ligands L, i.e. mixed ligand systems. These are described by compounds (9) to (26):

Compound (9)

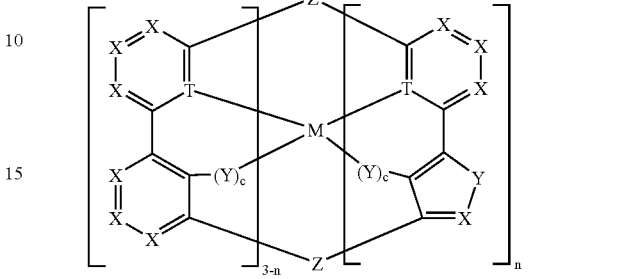

Compound (10)

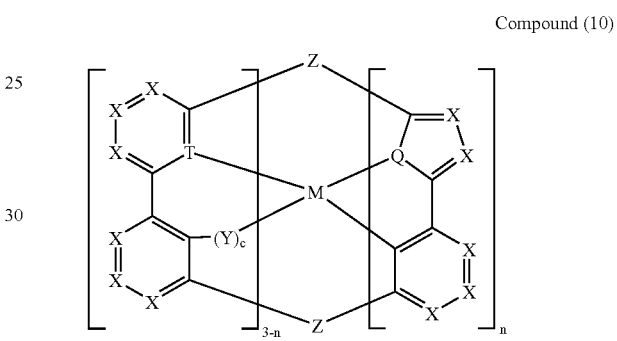

Compound (11)

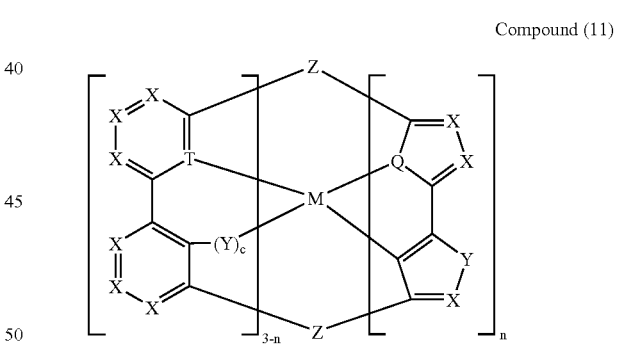

Compound (12)

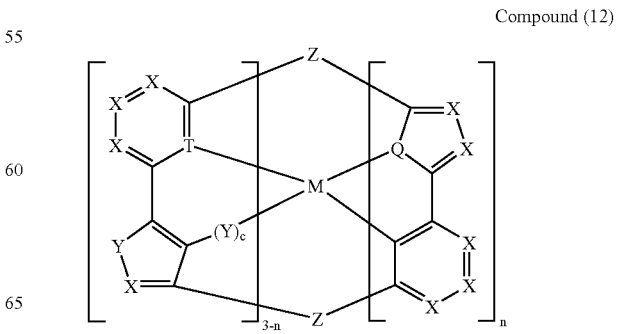

Compound (13)
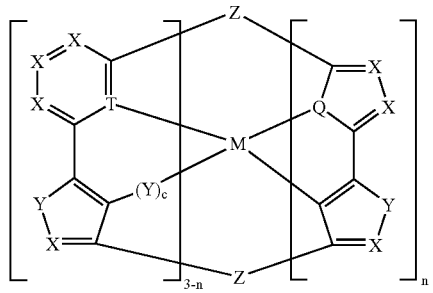
Compound (14)
Compound (15)
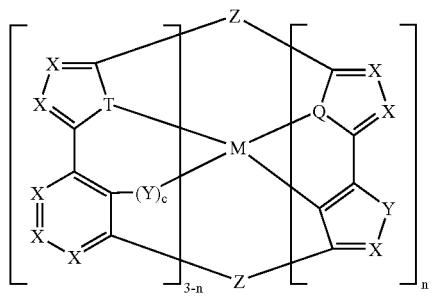
Compound (16)
Compound (17)
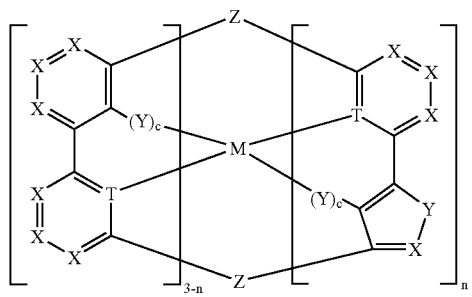
Compound (18)
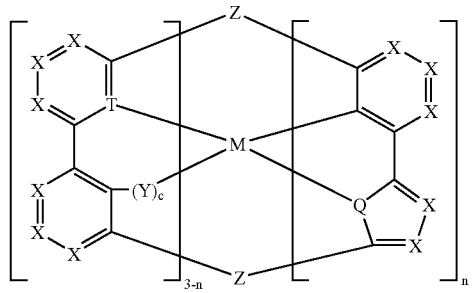
Compound (19)
Compound (20)
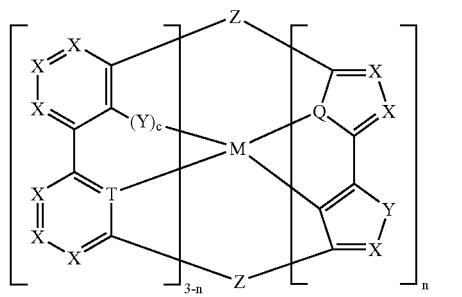
Compound (21)
Compound (22)
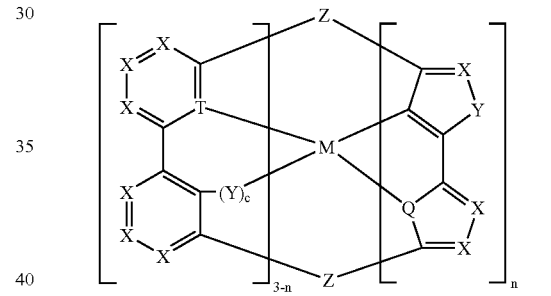
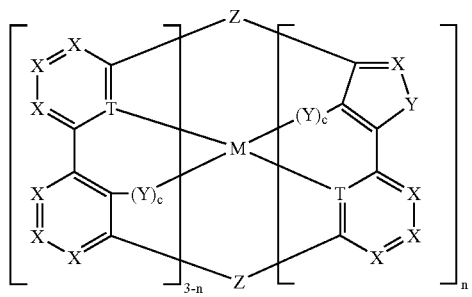
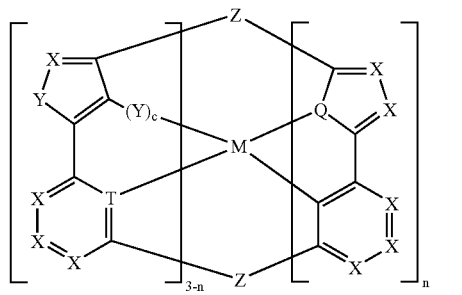

-continued

Compound (23)

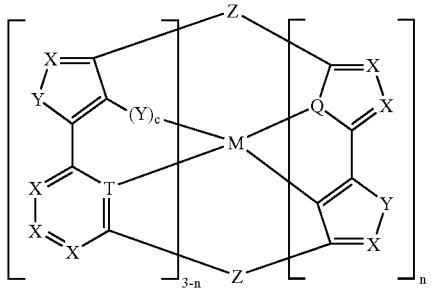

Compound (24)

Compound (25)

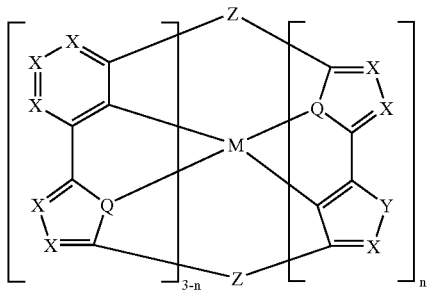

Compound (26)

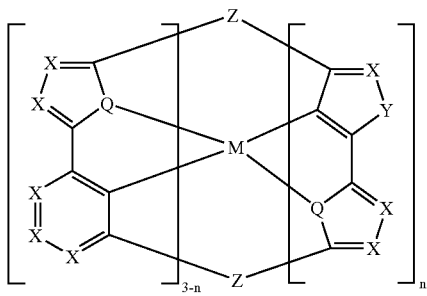

where the symbols and indices M, Q, T, X, Y, Z, R, $R^1$, c and n have the meanings indicated above.

Particular preference is given to compounds (1) to (26) according to the invention in which M on each occurrence, identically or differently, represents a transition-metal ion, very particularly preferably tungsten, rhenium, ruthenium, osmium, rhodium, iridium, palladium, platinum or gold.

Particular preference is furthermore given to compounds (1) to (26) according to the invention in which Q on each occurrence, identically or differently, represents O, S or Se, very particularly preferably O or S.

Particular preference is furthermore given to compounds (1) to (26) according to the invention in which T on each occurrence, identically or differently, represents N or P, very particularly preferably N.

Particular preference is furthermore given to compounds (1) to (26) according to the invention in which X on each occurrence, identically or differently, represents CR or N.

Particular preference is furthermore given to compounds (1) to (26) according to the invention in which Z on each occurrence, identically or differently, represents B, $BR^-$, $B(CR_2)_3$, $RB(CR_2)_3^-$, $B(O)_3$, $RB(O)_3^-$, $B(OCR_2)_3$, $RB(OCR_2)_3^-$, $Al(O)_3$, $RAl(O)_3^-$, $Al(OCR_2)_3$, $RAl(OCR_2)_3^-$, CR, $CNR^1{}_2$, $RC(CR_2)_3$, $RC(O)_3$, $RC(CR_2CR_2)_3$, $RC(CR_2O)_3$, $RC(OCR_2)_3$, SiR, $RSi(CR_2)_3$, $RSi(O)_3$, $RSi(CR_2CR_2)_3$, $RSi(OCR_2)_3$, $RSi(CR_2O)_3$, N, NO, $NR^+$, $N(CR_2)_3$, $RN(CR_2)_3^+$, $N(C=O)_3$, $N(CR_2CR_2)_3$, $RN(CR_2CR_2)^+$, P, PO, $P(O)_3$, $PO(O)_3$, $P(OCR_2)_3$, $PO(OCR_2)_3$, $S^+$, $S(CR_2)_3^+$, $S(CR_2CR_2)_3^+$, very particularly preferably $B(O)_3$, $RB(O)_3^-$, $B(OCR_2)_3$, $RB(OCR_2)_3^-$, $Al(O)_3$, $RAl(O)_3^-$, $Al(OCR_2)_3$, $RAl(OCR_2)_3^-$, $P(O)_3$, $P(OCR_2)_3$, $RC(CR_2)_3$, $RSi(O)_3$, $N(CR_2)_3$, $RN(CR_2)_3^+$.

Particular preference is furthermore given to compounds (1) to (26) according to the invention in which Y, identically or differently on each occurrence, represents O, S or $NR^1$, very particularly preferably O or S.

Particular preference is furthermore given to compounds (1) to (26) according to the invention in which R, identically or differently on each occurrence, represents H, F, Cl, Br, I, CN, a straight-chain, branched or cyclic alkyl or alkoxy group having 1 to 6 C atoms or an aryl or heteroaryl group having 3 to 8 C atoms, which may be substituted by one or more non-aromatic radicals R, where two or more substituents R, both on the same ring and also on the two different rings, may together in turn define a further mono- or polycyclic, aliphatic, aromatic and/or benzo-fused ring system.

Particular preference is furthermore given to compounds (1) to (26) according to the invention in which the index c on each occurrence is equal to 0.

The present invention likewise relates to the cryptands as described by compounds (27) to (52), which represent the ligands of the cryptates (1) to (26) according to the invention:

Compound (27)

-continued
Compound (28)
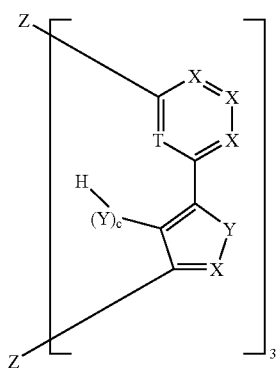
Compound (32)
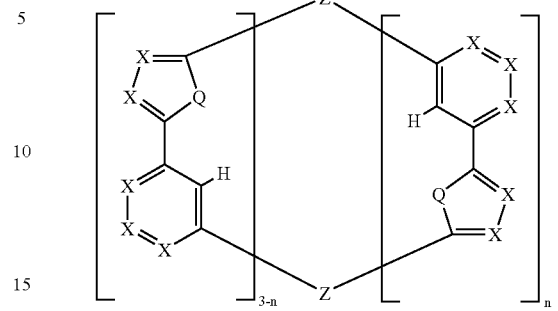
Compound (29)
Compound (33)
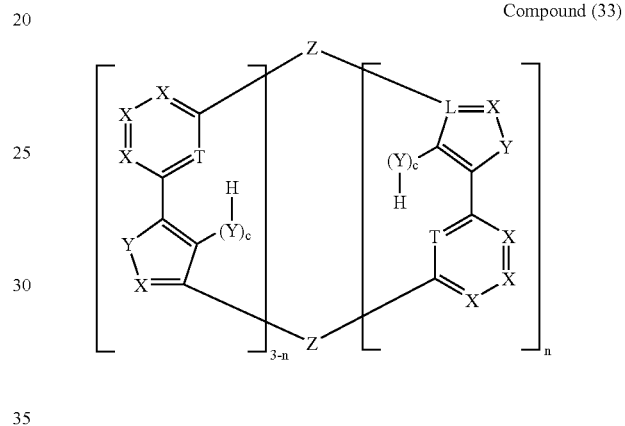
Compound (30)
Compound (34)
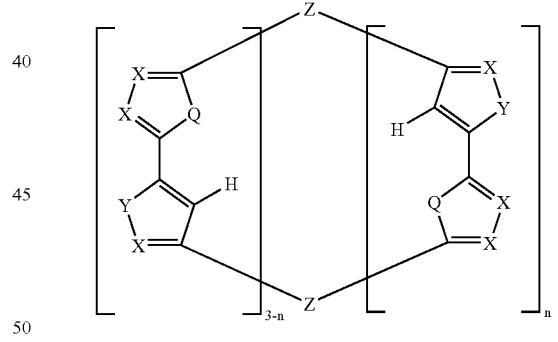
Compound (31)
Compound (35)
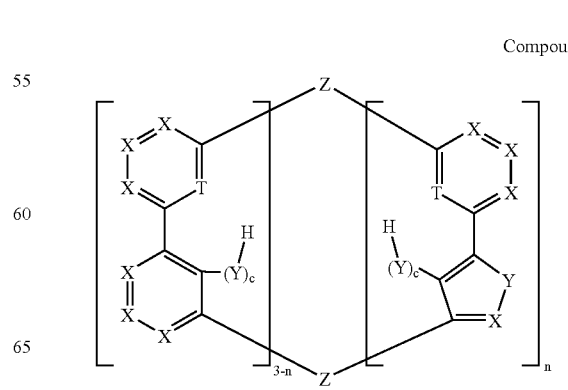

Compound (36)
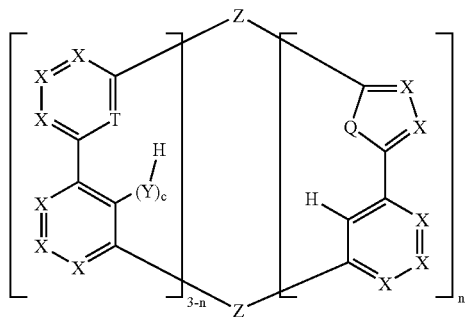
Compound (37)
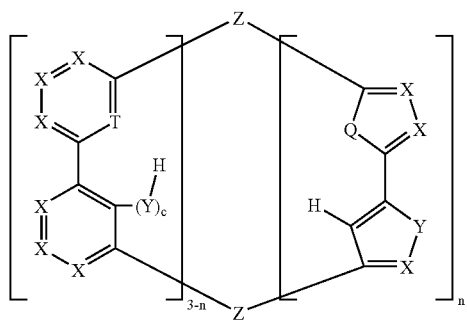
Compound (38)
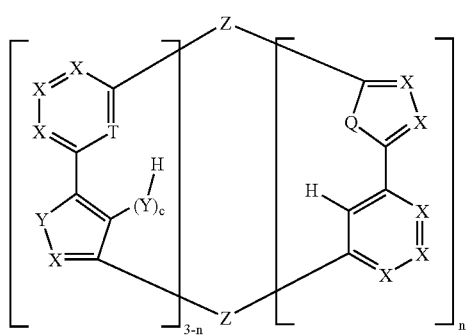
Compound (39)
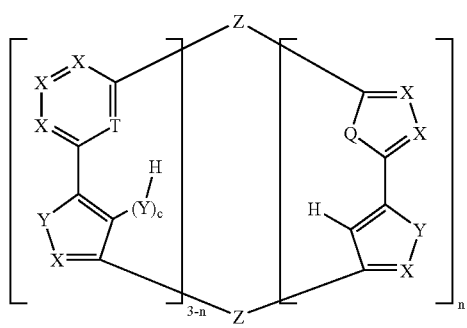
Compound (40)
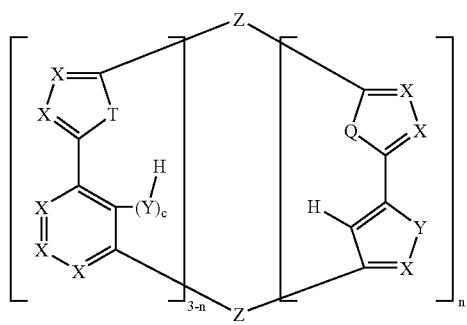
Compound (41)
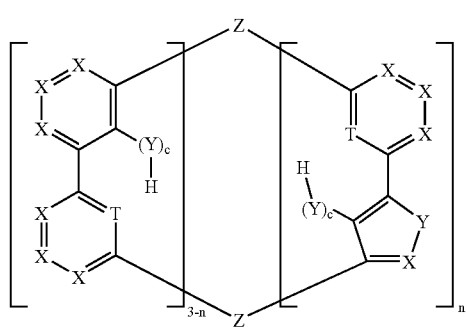
Compound (42)
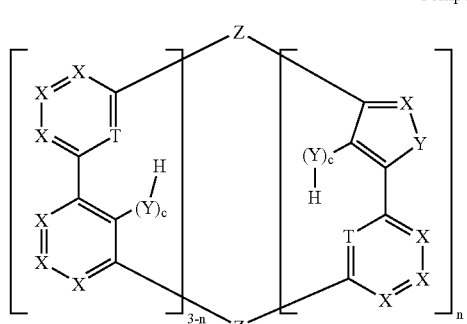
Compound (43)
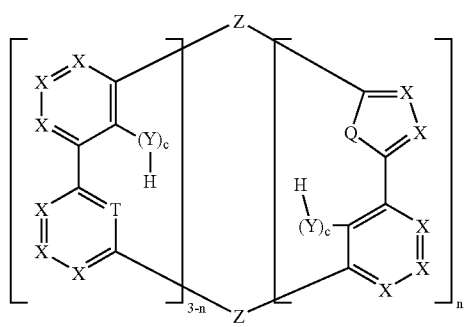

Compound (44)
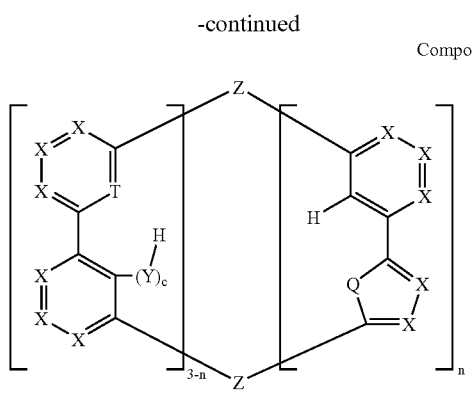
Compound (48)
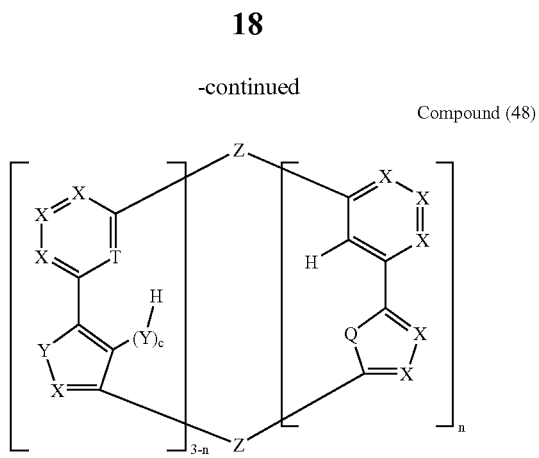
Compound (45)
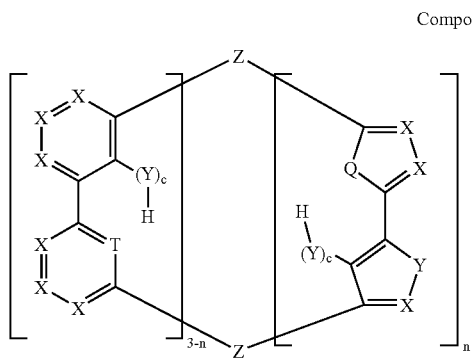
Compound (49)
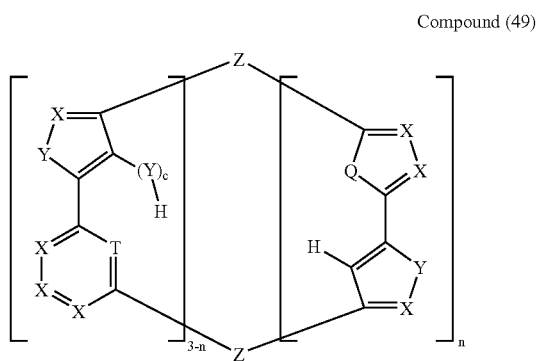
Compound (46)
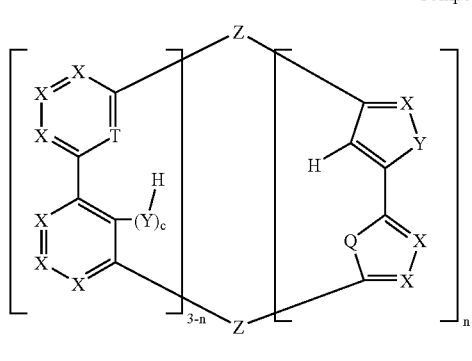
Compound (50)
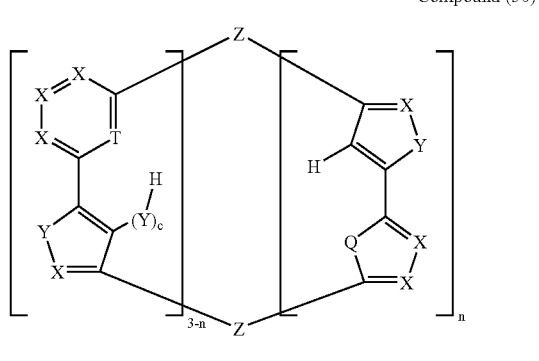
Compound (47)
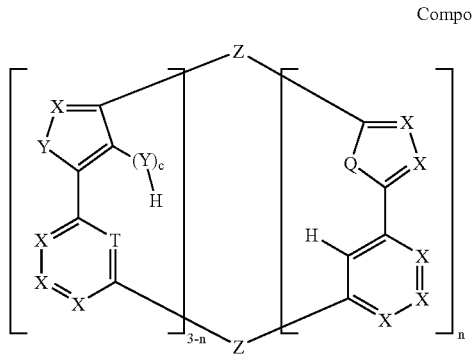
Compound (51)
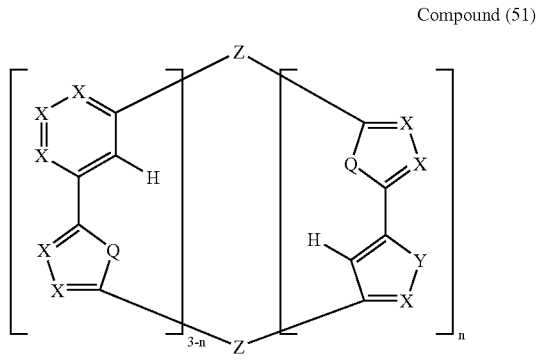

Compound (52)

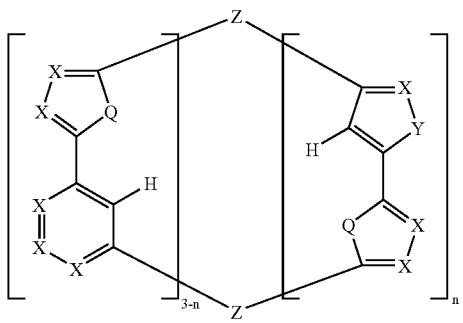

where the symbols and indices Q, T, X, Y, Z, R, $R^1$, c, n have the above-mentioned meanings.

Compounds (1) to (26) according to the invention can in principle be prepared by various processes, but where the processes described below have proven to be particularly suitable.

The present invention therefore furthermore relates to a process for the preparation of compounds (1) to (26) by reaction of the cryptands as described by compounds (27) to (52) or precursors of these cryptands with metal alkoxides as described by compound (53), with metal ketoketonates as described by compound (54) or metal halides as described by compound (55)

Compound (53)

$M(OR^1)_p$

Compound (54)

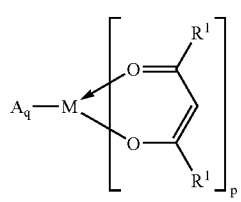

Compound (55)

$MHal_p$ where the following applies to the symbols and indices:

M is on each occurrence, identically or differently, a main-group metal ion, a transition-metal ion or a lanthanoid ion;

Hal is on each occurrence, identically or differently, F, Cl, Br or I;

A is on each occurrence, identically or differently, a neutral or monoanionic, monodentate or bidentate ligand, for example a halide;

p is on each occurrence, identically or differently, 1, 2, 3, 4 or 5, where p in compounds (53) and (55) indicates the valency of the metal M;

q is on each occurrence, identically or differently, 0, 1, 2, 3 or 4, preferably 0, 1 or 2;

compound (54) here may also be charged and may also contain a counterion; the other symbols and indices have the same meaning as indicated above.

The synthesis can be activated, for example, thermally, photochemically or by microwave radiation. The synthesis of tris-ortho-metallated metal complexes of this type is described in general terms in WO 02/060910, WO 04/085449, and WO 04/108738.

In a preferred synthetic process, the cryptand as described by compounds (27) to (52) is reacted with metal compounds, as described by compounds (53), (54) and (55). This synthetic process is depicted diagrammatically in Scheme 2:

Scheme 2:

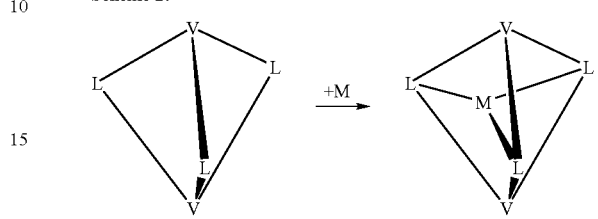

A further preferred synthetic process for the cryptates according to the invention has proven to be template synthesis. To this end, metal compounds, as described above by compounds (53), (54) and (55), are reacted with a simple, macrocyclic or polypodal precursor of ligands (27) to (52), where the ligand precursor is derived from the ligand in that it contains no or only one bridging unit V or Z instead of two or in that it contains only two part-ligands L instead of three. Corresponding polypodal ligand systems and complexes are described, for example, in WO 04/081017. In a second synthesis step, the second bridging unit V or Z is then introduced in a complex-analogous reaction, i.e. a reaction at the metal complex, or both bridging units V or Z are formed, or the third part-ligand L is introduced and linked to the bridging units V or Z. These synthetic methods have the advantage that the fact that the complex formation has already taken place means that the three part-ligands L are already present in a spatially preferred arrangement which enables simple ring closure for the introduction of V or Z or for the linking of the third part-ligand, which is only possible with considerable technical complexity and in poor yields using the uncomplexed polypodal ligand. These synthetic methods are depicted diagrammatically in scheme 3.

Particular preference is given to the synthesis starting from the corresponding polypodal ligand.

Scheme 3:

Synthesis with formation of a bridging unit V:

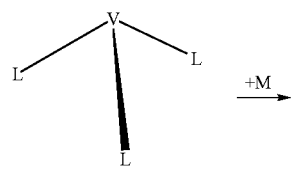

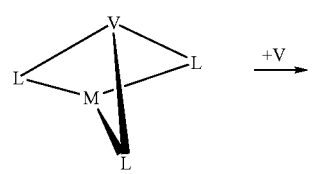

-continued

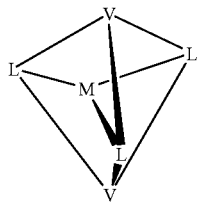

Synthesis with formation of two bridging units V:

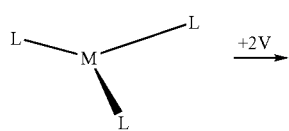

Synthesis with introduction and linking of the third part-ligand:

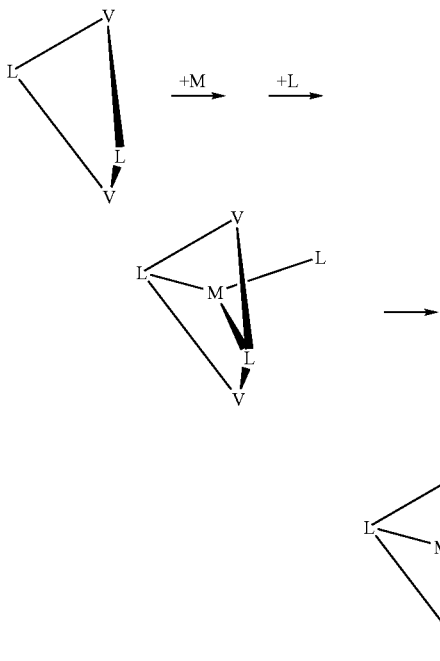

These processes easily give the complexes in high purity, preferably in a purity of >99%, determined by $^1$H-NMR or HPLC.

The synthetic methods explained here enable the preparation of, inter alia, the examples of compounds (1) to (26) depicted below.

Example 1

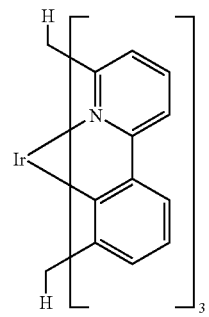

Example 2

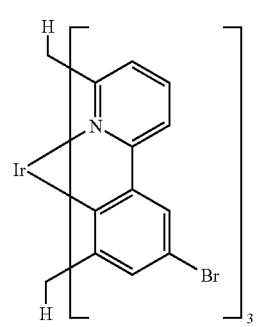

Example 3

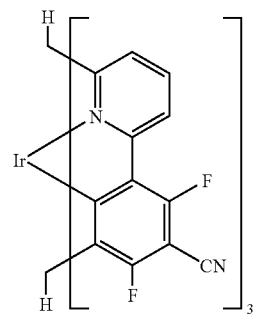

Example 4

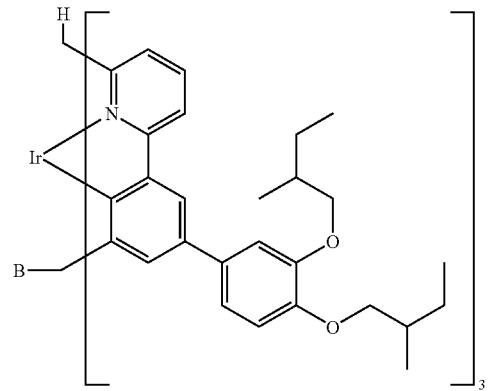

-continued
Example 5
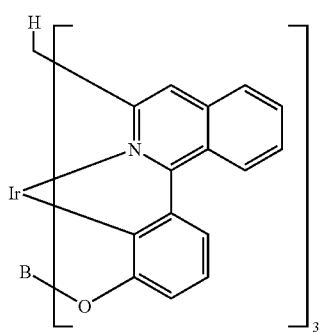
Example 6
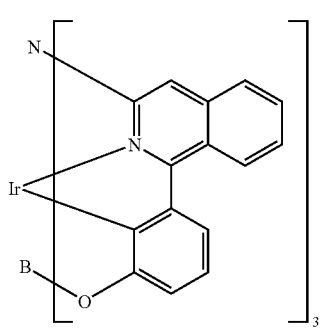
Example 7
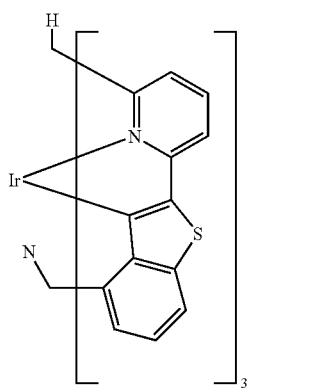
Example 8
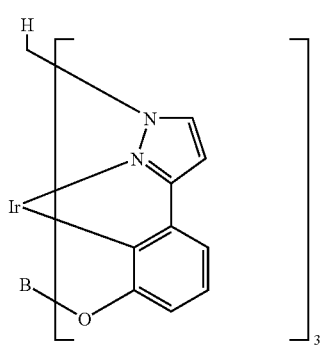
-continued
Example 9
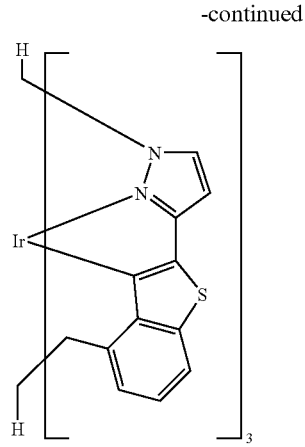
Example 10
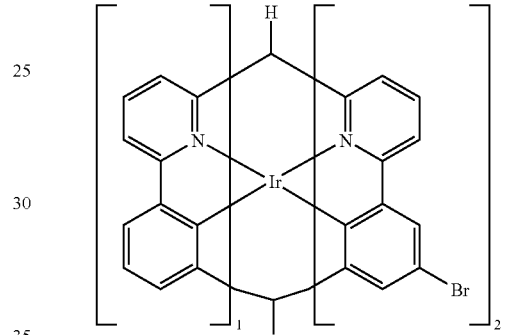
Example 11
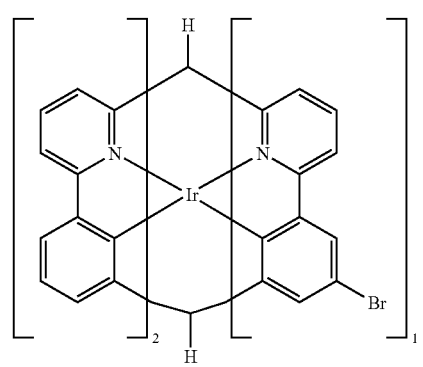
Example 12
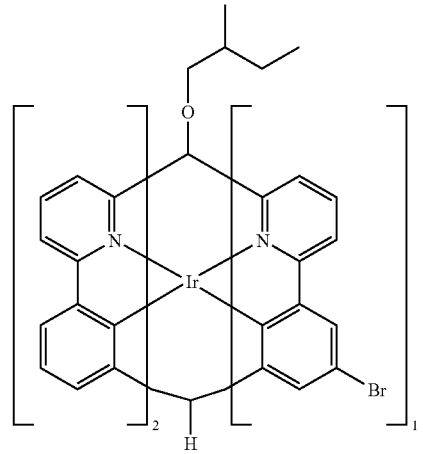

-continued
Example 13
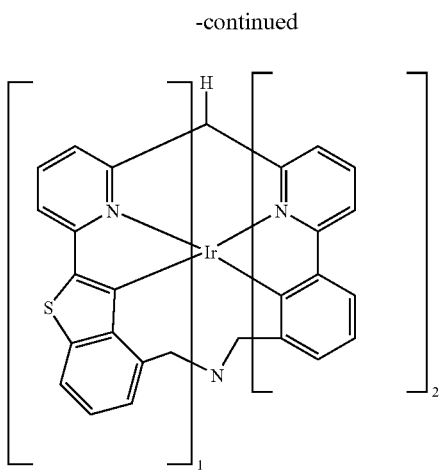
Example 14
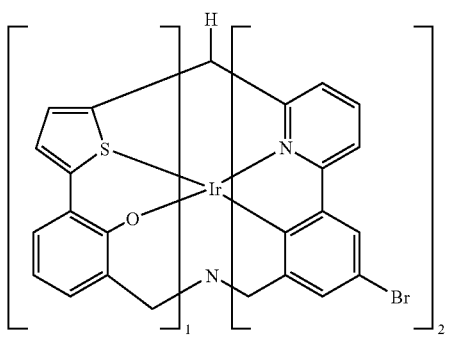
Example 15
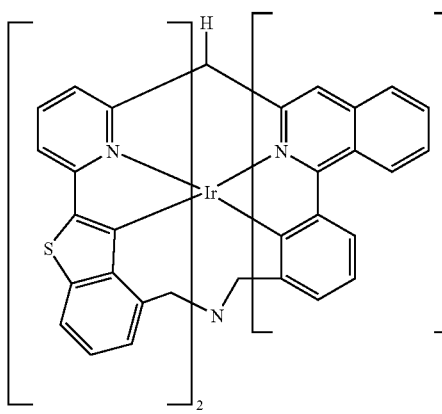
Example 16
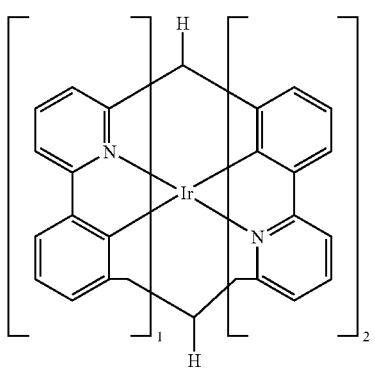
Example 17
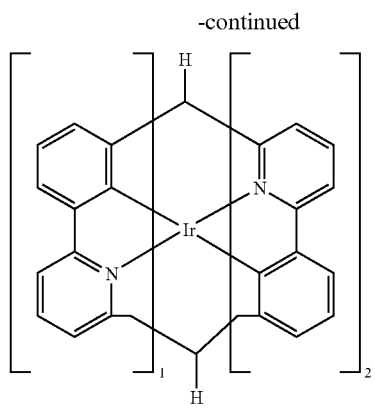
Example 18
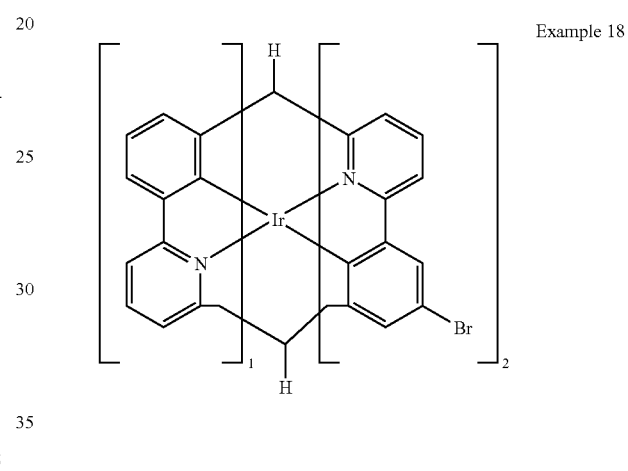
Example 19
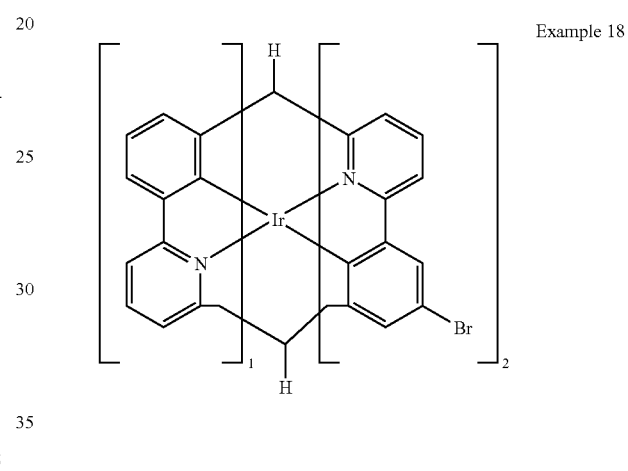
Example 20
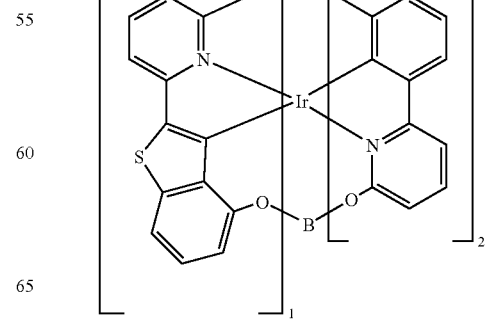

-continued
Example 21
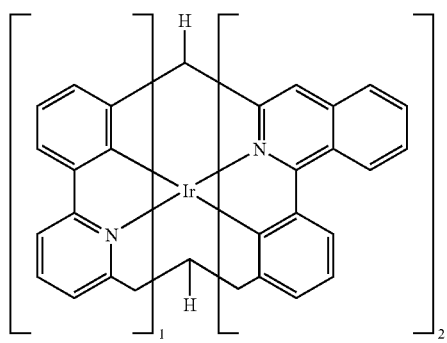
Example 22
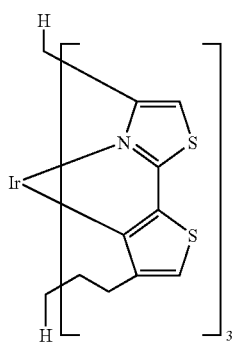
Example 23
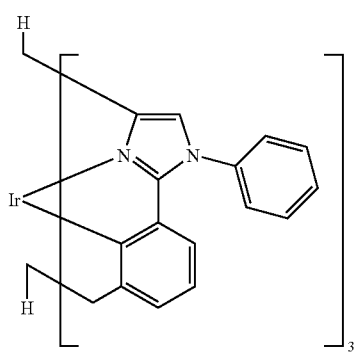
Example 24
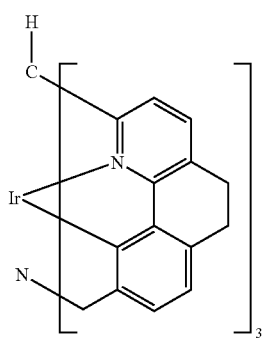
-continued
Example 25
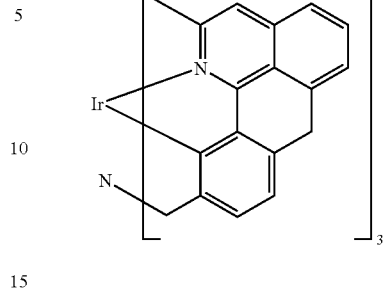
Example 26
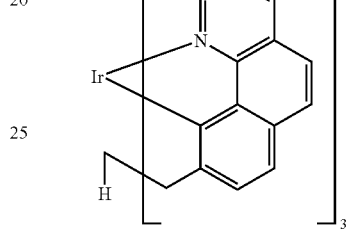
Example 27
Example 28
Example 29
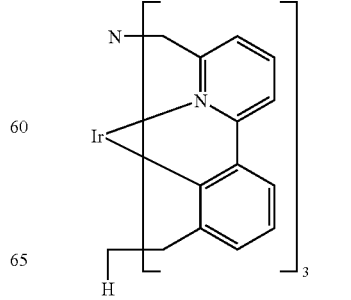

-continued
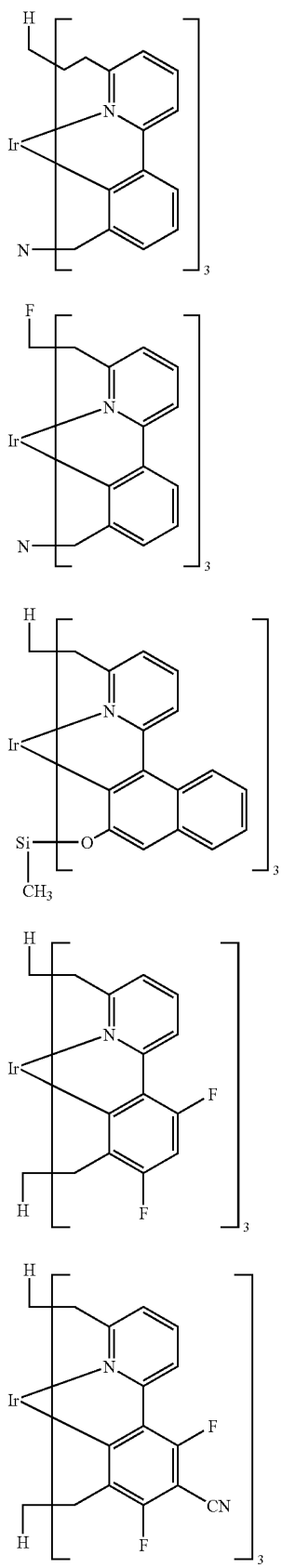
Example 30
Example 31
Example 32
Example 33
Example 34
-continued
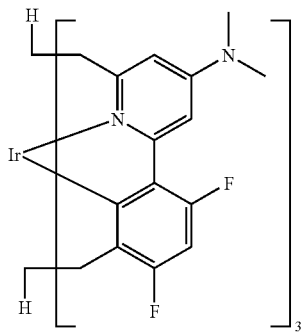
Example 35
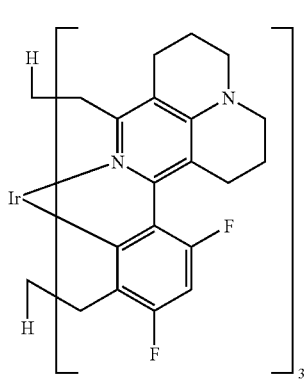
Example 36
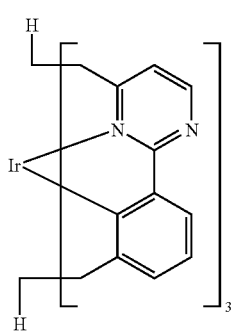
Example 37
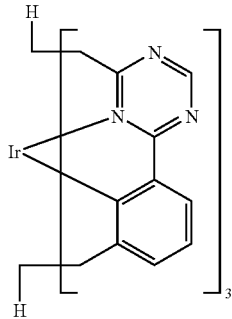
Example 38

-continued
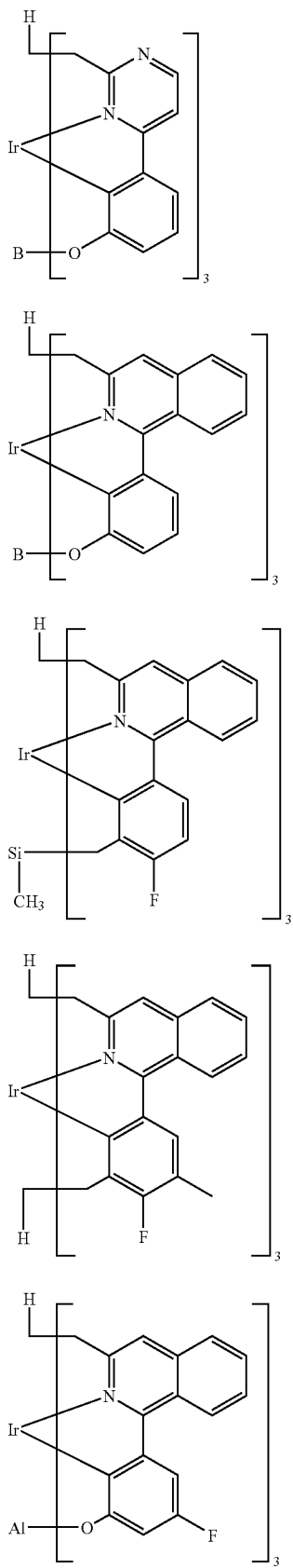
Example 39
Example 40
Example 41
Example 42
Example 43
-continued
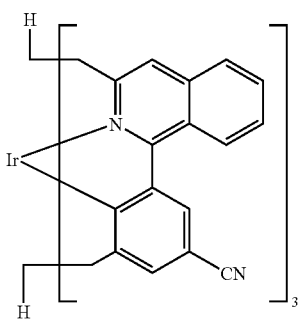
Example 44
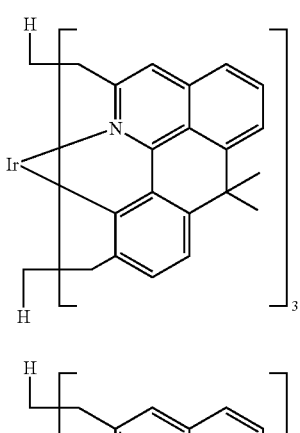
Example 45
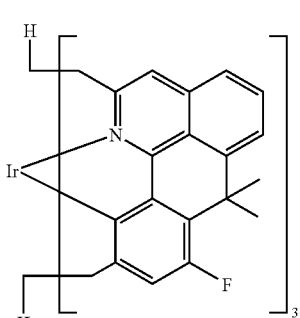
Example 46
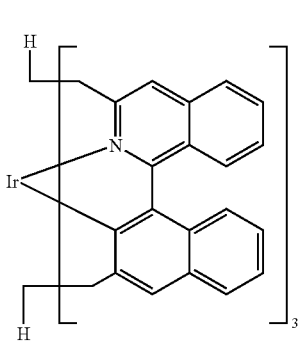
Example 47
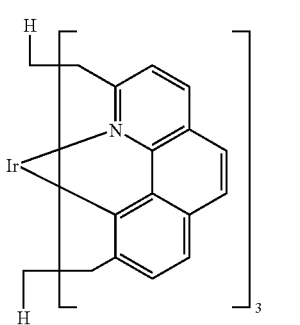
Example 48

Example 49
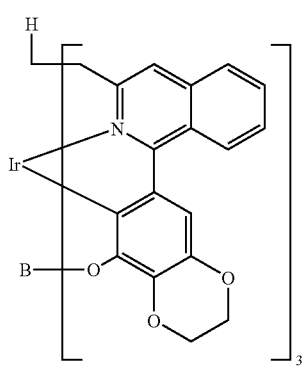
Example 50
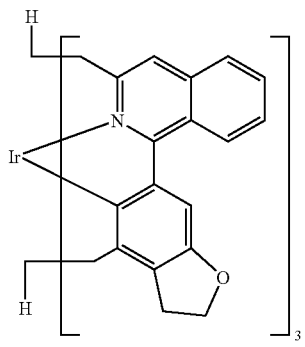
Example 51
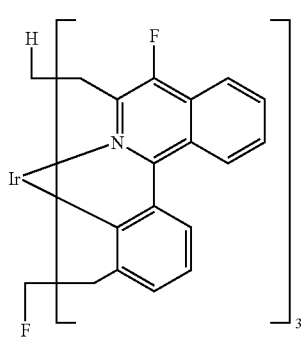
Example 52
Example 53
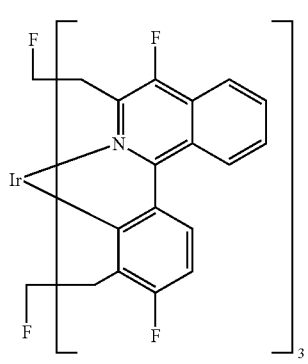
Example 54
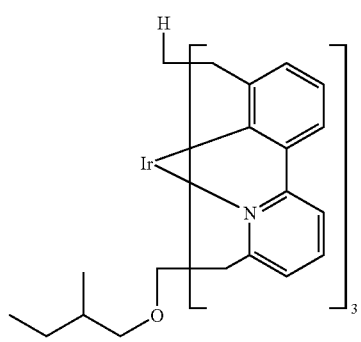
Example 55
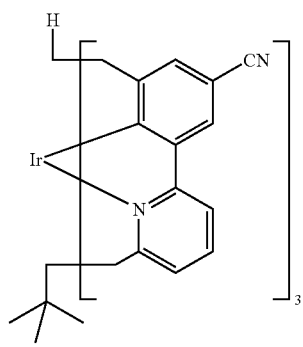
Example 56
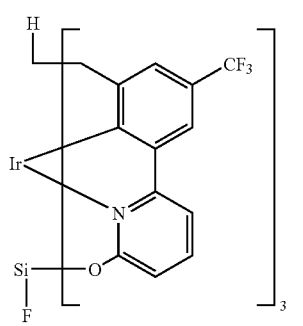

Example 57
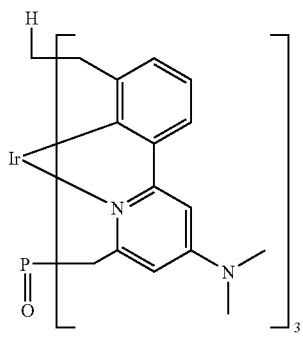
Example 58
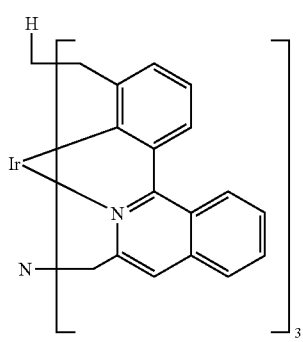
Example 59
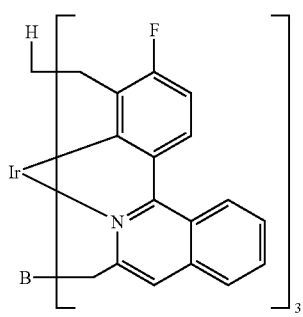
Example 60
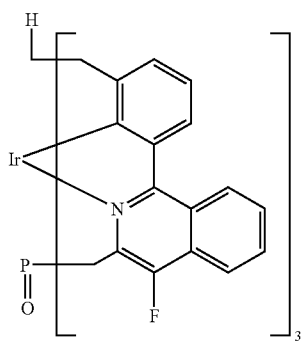
Example 61
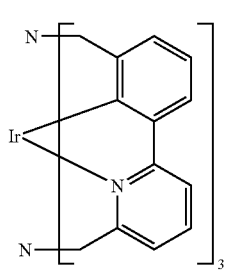
Example 62
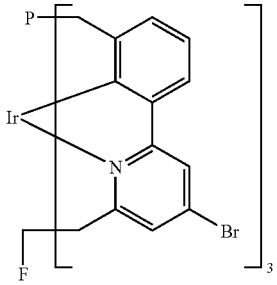
Example 63
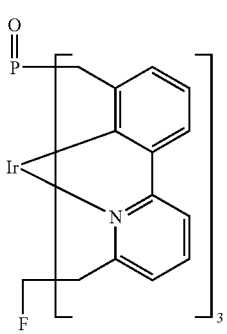
Example 64
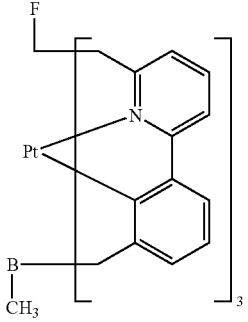
Example 65
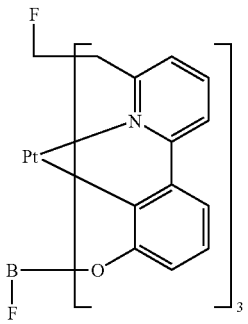
Example 66
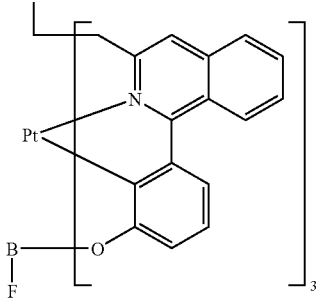

The compounds according to the invention described above, for example compounds as described by Examples 10, 11, 12, 14 and 18, can also be used as co-monomers for the production of conjugated, partially conjugated or non-conjugated polymers or as the core of dendrimers, for example compounds as described by Examples 2 and 62. The corresponding polymerisation is preferably carried out here via the halogen functionality. Thus, they can be copolymerised, inter alia, into soluble polyfluorenes (for example in accordance with EP 842208, WO 00/22026), polyspirobifluorenes (for example in accordance with EP 707020, EP 894107), poly-para-phenylenes (for example in accordance with WO 92/18552), polydihydrophenanthrenes (for example in accordance with WO 05/014689), polyphenanthrenes (for example in accordance with the unpublished application DE 102004020298.2), polycarbazoles (for example in accordance with WO 04/070772, WO 04/113468), polyvinylcarbazoles, polythiophenes (for example in accordance with EP 1028136), silane-containing polymers (for example the unpublished application DE 102004023278.4) or also copolymers comprising a plurality of these units.

The invention thus furthermore relates to conjugated, partially conjugated and non-conjugated polymers or dendrimers containing one or more cryptates of the formula (1) or compounds (1) to (26), where one or more of the substituents R defined above represent a bond to the polymer or dendrimer.

The metal complexes according to the invention may furthermore also be functionalised and thus converted into extended metal complexes. Examples which may be mentioned here are the SUZUKI functionalisation using arylboronic acids and the HARTWIG-BUCHWALD functionalisation using amines.

The compounds, polymers or dendrimers according to the invention described above are used as active components in electronic components, such as, for example, organic light-emitting diodes (OLEDs), organic integrated circuits (O-ICs), organic field-effect transistors (OFETs), organic thin-film transistors (OTFTs), organic solar cells (O-SCs), organic optical detectors or organic laser diodes (O-lasers).

Active components are, for example, charge-injection or charge-transport materials, charge-blocking materials and emission materials. The compounds are particularly preferably employed as emission materials.

The invention thus furthermore relates to the use of cryptates in electronic components. Preference is given to the use of organometallic cryptates of the formula (1), particular preference is given to the use of compounds (1) to (26).

The invention furthermore relates to organic electronic components, such as, for example, organic integrated circuits (O-ICs), organic field-effect transistors (OFETs), organic thin-film transistors (OTFTs), organic solar cells (O-SCs), organic optical detectors or organic laser diodes (O-lasers), but in particular organic light-emitting diodes (OLEDs), comprising one or more cryptates. Preference is given to organic electronic components comprising one or more organometallic cryptates of the formula (1). Particular preference is given to organic electronic components comprising one or more cryptates as described by compounds (1) to (26), where the above-mentioned preferences for compounds (1) to (26) also apply to the electronic components.

The compounds are distinguished by the following advantages:

1. In contrast to many metal complexes in accordance with the prior art, which undergo partial or complete pyrolytic decomposition on sublimation, the compounds according to the invention have high thermal stability. On use in corresponding devices, this results in a significant increase in the operating lifetime.
2. The compounds according to the invention can be prepared reproducibly in reliable, high purity and have no batch variations. They can furthermore be sublimed without difficulties and without evident decomposition for purification or for production of the electronic device. The high thermal stability of the complexes enables resource-conserving use thereof.
3. The compounds according to the invention, employed in electroluminescent devices, result in high efficiencies and in steep current/voltage curves.
4. The compounds according to the invention have good, in some cases excellent solubility in organic solvents. These materials can thus be purified more easily from solution, for example by recrystallisation, chromatography, etc., and they can also be processed from solution by coating or printing techniques. This property is also advantageous in the case of conventional processing by evaporation since the cleaning of the equipment and the shadow masks employed is thus considerably simplified.
5. The compounds according to the invention have higher oxygen stability than complexes in accordance with the prior art. Industrial handling of these complexes is thus considerably simplified.

The present invention is explained in greater detail by the following examples without wishing to be restricted thereto. The person skilled in the art will be able to prepare further cryptates according to the invention from the descriptions without inventive step and use these in organic electronic devices.

EXAMPLE

The following syntheses were carried out under a protective-gas atmosphere, unless indicated otherwise. The starting materials were purchased from ALDRICH or ABCR (solvents, 3-bromobenzyl bromide, hydrogen bromide in glacial acetic acid, zinc, 2-bromo-6-methoxypyridine, pyridinium hydrochloride, borane-1M in THF, sodium dichlorodiacetylacetonatoiridium(III)). 3-Bromobenzylphosphonium bromide (Organikum [Practical Organic Chemistry], 19th Edition, 1993, Johann Ambrosius Barth Verlagsgesellschaft, Edition Deutscher Verlag der Wissenschaften, Leipzig, Berlin, Heidelberg, p. 215) and bis(3-bromobenzyl)ketone (H. Sauriat-Dorizon et al., *J. Org. Chem.*, 2003, 68, 2, 240.) were prepared by literature methods.

Example 1

1,1,2-Tris(3-bromobenzyl)ethene

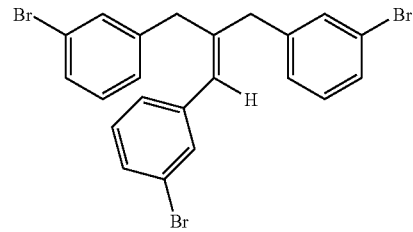

164.2 g (320 mmol) of 3-bromobenzyltriphenylphosphonium bromide were added to a suspension of 7.2 g (300 mmol) of sodium hydride in 2000 ml of toluene. This mixture was stirred at 80° C. for 3 h. A solution of 110.4 g (300 mmol) of bis(3-bromobenzyl)ketone in 500 ml of toluene was subsequently added dropwise, and the mixture was stirred at 80° C. for a further 48 h. After the reaction mixture had been cooled, the precipitate formed was filtered off with suction. The precipitate was washed with 100 ml of toluene, and the combined organic phases were evaporated to dryness. The residue was taken up in 1000 ml of n-hexane, the hexane was decanted off, and the residue was again extracted twice with 300 ml of n-hexane each time. The combined hexane phases were concentrated to a volume of about 500 ml and filtered through 200 g of aluminium oxide (activity grade 4). The filtrate was evaporated, leaving the product as a pale-yellow oil. The yield, with a purity of about 97%, was 152.3 g (292 mmol), corresponding to 97.4% of theory.

$^1$H-NMR (CDCl$_3$): δ [ppm]=7.42-7.34 (m, 4H), 7.30-7.22 (m, 2H), 7.19-7.14 (m, 4H), 7.08-7.00 (m, 2H), 6.49 (s, 1H, CH), 3.47 (s, 2H, CH$_2$), 3.32 (s, 2H, CH$_2$).

Example 2

Tris(3-bromobenzyl)bromomethane

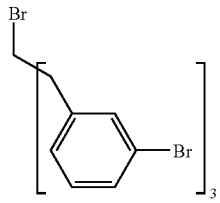

500 ml of a 30% by weight solution of hydrogen bromide in glacial acetic acid were added dropwise to a solution of 140.7 g (270 mmol) of 1,1,2-tris(3-bromobenzyl)-ethene in 1000 ml of glacial acetic acid. After the mixture had been stirred at room temperature for 48 h, the colourless precipitate was filtered off with suction, washed twice with 200 ml of glacial acetic acid each time and subsequently dried under reduced pressure. The yield, with a purity of about 97%, was 157.2 g (261 mmol), corresponding to 96.7% of theory.

$^1$H-NMR (CDCl$_3$): δ [ppm]=7.45 (s, 3H, H-2), 7.42 (d, $^3J_{HH}$=8.0 Hz, 3H, H-4), 7.22 (d, $^3J_{HH}$=8.0 Hz, 3H, H-6), 7.18 (dd, $^3J_{HH}$=8.0 Hz, 3H, H-5), 3.04 (s, 6H, CH$_2$).

Example 3

Tris(3-bromobenzyl)methane

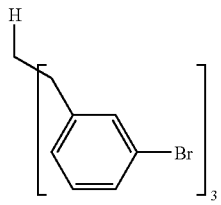

A suspension of 150.5 g (250 mmol) of tris(3-bromobenzyl)bromomethane and 163.5 g (2.5 mol) of zinc dust in 2000 ml of glacial acetic acid was stirred at 50° C. for 6 h. After cooling, the reaction mixture was filtered through silica gel (care: the filter residue is pyrophoric!). The filtrate was freed from glacial acetic acid under reduced pressure, and the residue was taken up in 1000 ml of dichloromethane. After the dichloromethane phase had been washed with water (2×500 ml), dried over sodium sulfate/sodium hydrogencarbonate and evaporated, the residue was freed from final traces of water by taking up in 500 ml of toluene and removal of the toluene by azeotropic distillation. The yield, with a purity of about 97%, was 122.9 g (235 mmol), corresponding to 94.0% of theory.

$^1$H-NMR (CDCl$_3$): δ [ppm]=7.29 (d, $^3J_{HH}$=8.0 Hz, 3H, H-4), 7.19 (s, 3H, H-2), 7.10 (dd, $^3J_{HH}$=8.0 Hz, 3H, H-5), 6.97 (d, $^3J_{HH}$=8.0 Hz, 3H, H-6), 2.46 (d, $^3J_{HH}$=7.0 Hz, 6H, CH$_2$), 2.19 (sep., $^3J_{HH}$=7.0 Hz, 1H, CH).

Example 4

Tris(benzyl-3-boronic acid)methane

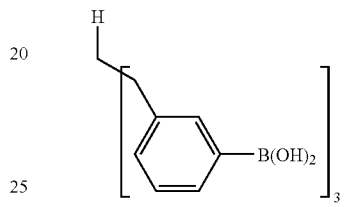

The corresponding Grignard reagent was prepared from a solution of 120.3 g (230 mmol) of tris(3-bromobenzyl)methane and 5.4 ml (69 mmol) of 1,2-dichloroethane in 1000 ml of THF and 18.6 g (765 mmol) of magnesium (etched with one grain of iodine). The Grignard reagent was added dropwise over the course of 1 h to a mixture, cooled to −78° C., of 111.5 ml (995 mmol) of trimethyl borate and 600 ml of THF, during which the temperature did not exceed −60° C. After slow (about 12 h) warming of the reaction mixture to RT, a mixture of 80 ml of conc. HCl and 400 ml of water was added. After stirring for 30 min., the organic phase was separated off and washed with 500 ml of sat. sodium chloride solution. The organic phase was evaporated to dryness. The oily residue was recrystallised from 400 ml of acetonitrile and 1000 ml of water at the boiling point. The yield, with a purity of about 97%, was 81.1 g (194 mmol), corresponding to 84.3% of theory.

$^1$H-NMR (DMSO): δ [ppm]=7.97 (br. s, 6H, OH), 7.61 (d, $^3J_{HH}$=7.6 Hz, 3H, H-4), 7.57 (s, 3H, H-2), 7.26 (dd, $^3J_{HH}$=7.6 Hz, 3H, H-5), 7.16 (d, $^3J_{HH}$=7.6 Hz, 3H, H-6), 2.47 (d, $^3J_{HH}$=6.7 Hz, 6H, CH$_2$), 2.28 (sep., $^3J_{HH}$=6.7 Hz, 1H, CH).

Example 5

Tris(3-(6-methoxy-2-pyridyl)benzyl)methane

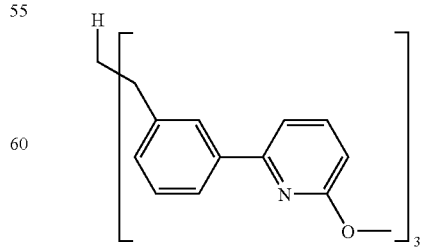

347 mg (0.3 mmol) of tetrakis(triphenylphosphino)palladium(0) were added to a degassed suspension of 4.18 g (10 mmol) of tris(benzyl-3-boronic acid)methane, 5.5 ml (45 mmol) of 2-bromo-6-methoxypyridine and 9.54 g (90 mmol) of sodium carbonate in a mixture of 120 ml of 1,2-dimethoxyethane, 30 ml of ethanol and 90 ml of water, and the mixture was refluxed for 48 h. 500 ml of dichloromethane were added to the cooled reaction mixture, which was washed five times with 500 ml of water. Chromatography of the organic phase, which had been dried over sodium sulfate and evaporated, over silica gel using hexane:ethyl acetate (1:1) gave 5.0 g (8.3 mmol), corresponding to 83.1% of theory, of a pale-yellow oil.

$^1$H-NMR (CDCl$_3$): δ [ppm]=7.78 (m, 6H), 7.65 (m, 6H), 7.35 (dd, $^3J_{HH}$=8.0 Hz, 3H), 7.21-7.14 (m, 6H), 3.92 (s, 9H, CH$_3$), 2.76 (d, $^3J_{HH}$=7.0 Hz, 6H, CH$_2$), 2.52 (sep., $^3J_{HH}$=7.0 Hz, 1H, CH).

Example 6

Tris(3-(6-hydroxy-2-pyridyl)benzyl)methane

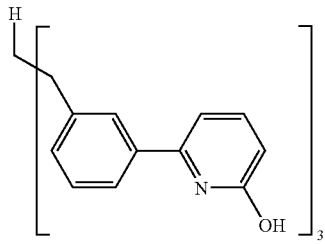

A mixture of 4.9 g (8.0 mmol) of tris(3-(6-methoxy-2-pyridyl)benzyl)methane and 7.4 g (64 mmol) of pyridinium hydrochloride was heated at 190° C. for 3 h. After cooling, the mixture was taken up in 200 ml of water and adjusted to pH=7.7 using 1N potassium hydroxide solution. The aqueous phase was extracted five times with 200 ml of dichloromethane. The organic phase was dried over magnesium sulfate and filtered through a short frit with silica gel. After removal of the solvent, the residue was recrystallised from tert-butyl methyl ether:n-heptane (1:2). The yield, with a purity of about 97%, was 3.8 g (6.7 mmol), corresponding to 83.8% of theory.

$^1$H-NMR (CDCl$_3$): δ [ppm]=11.44 (br. s, 3H), 7.88 (m, 6H), 7.70 (m, 6H), 7.39 (dd, $^3J_{HH}$=8.0 Hz, 3H), 7.26-7.13 (m, 6H), 2.78 (d, $^3J_{HH}$=7.0 Hz, 6H, CH$_2$), 2.51 (sep., $^3J_{HH}$=7.0 Hz, 1H, CH).

Example 7

Mono[tris(3-(6-hydroxy-2-pyridyl)benzyl)methane]iridium(III)

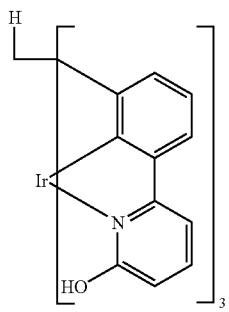

A suspension of 2.83 g (5 mmol) of tris(3-(6-hydroxy-2-pyridyl)benzyl)methane and 2.42 g (5 mmol) of sodium dichlorodiacetylacetonatoiridium(III) in 100 ml of triethylene glycol was stirred at an oil-bath temperature of 220° C. for 40 h. After the reaction mixture had been cooled to 60° C., it was poured into a mixture of 100 ml of 5N hydrochloric acid and 500 ml of ethanol, and the suspension formed in this way was stirred for a further 1 h. The yellow, microcrystalline solid was then filtered off with suction (P3). This solid was washed three times with 50 ml of a mixture of 100 ml of 5N hydrochloric acid and 500 ml of ethanol each time, three times with 50 ml of a water/ethanol mixture (1:1, v:v) each time and finally three times with 50 ml of ethanol each time and dried under reduced pressure. The yield, with a purity of about 99.5%, was 1.84 g (2.4 mmol), corresponding to 48.8% of theory.

MS (FAB): m/e=755.

Example 8

Synthesis of the Cryptate K1

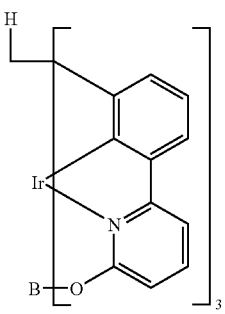

5 ml of a 1M solution of borane in THF were added dropwise to a suspension of 1.51 g (2 mmol) of mono[tris(3-(6-hydroxy-2-pyridyl)benzyl)methane]iridium(III) in 300 ml of THF, and the mixture was stirred at room temperature for 24 h. After addition of 5 ml of ethanol, the suspension was concentrated to a volume of 30 ml, and a further 100 ml of ethanol were added. The yellow precipitate was filtered off with suction (P3), washed five times with 30 ml of ethanol, dried under reduced pressure, recrystallised from DMF and sublimed at 420° C. in a high vacuum (p=5×10$^{-5}$ mbar). The yield, with a purity of 99.9% according to HPLC, was 1.19 g (1.5 mmol), corresponding to 76.7% of theory.

MS (FAB): m/e=763.

Example 9

Comparison of the Thermal Stability

The cryptate described in Example 8 (molecular weight 762.7 g/mol) was sublimed at 420° C. under reduced pressure (p=5×10$^{-5}$ mbar). The sublimation proceeded without leaving a residue and without signs of decomposition, checked by means of HPLC. Storage experiments at 400° C. for 160 h in sealed-off ampoules likewise gave no indication of thermally induced decomposition of the cryptate according to Example 8.

By comparison, the analogous, non-cryptate iridium complex Ir(PPy)$_3$ (fac-tris(2-(2-pyridinyl)phenyl)iridium, CAS: 94928-86-6, comparative example in accordance with the prior art, molecular weight=654.8 g/mol) has significantly lower stability. Sublimation of this complex with an initial purity of greater than 99.9% according to $^1$H-NMR and HPLC at T=360° C. and p=5×10$^{-5}$ mbar gave after 2 h:

about 5% by weight of an iridium-containing ash, about 94% by weight of a yellow sublimate, traces of an organic condensate, comprising, inter alia, 2-phenylpyridine, determined by $^1$H-NMR.

The yellow sublimate was not uniform. According to $^1$H-NMR and HPLC analysis, it consisted of a mixture of various species. The purity was about 99.6% of Ir(PPy)$_3$. Storage experiments at 340° C. for 160 h resulted in substantial decomposition of the complex in accordance with the prior art.

These results show that the cryptate according to Example 8 according to the invention has excellent long-term stability and is therefore extremely suitable for industrial use. In particular, the stability of the cryptate according to Example 8 according to the invention is significantly higher than that of the comparative complex in accordance with the prior art.

The invention claimed is:

1. An organometallic cryptate of the formula (1)

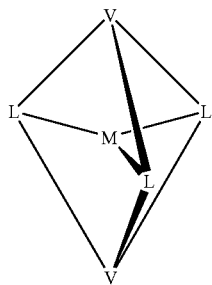

Formula (1)

containing at least one metal M coordinated to a cryptand K of the formula (2)

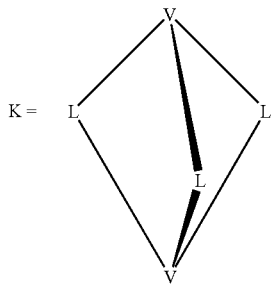

Formula (2)

where V is a bridging unit, identically or differently on each occurrence, containing 1 to 80 atoms which covalently bonds the three part-ligands L, which may be identical or different on each occurrence, to one another; the three part-ligands L are described by the formula (3)

Formula (3)

where DCy is a substituted or unsubstituted cyclic group which contains at least one donor atom in the ring or exocyclically bonded, via which atom the cyclic group DCy is bonded to the metal, and CCy is a substituted or unsubstituted cyclic group which contains at least one carbon atom, via which the cyclic group CCy is bonded to the metal; the groups DCy and CCy are bonded to one another via a covalent bond and may additionally be linked to one another via substituents and thus define a polycyclic, aliphatic or aromatic ring system.

2. The organometallic cryptate according to claim 1, wherein the cryptates are electrically neutral.

3. The organometallic cryptate according to claim 1, wherein all three part-ligands L in the complex are singly negatively charged.

4. The organometallic cryptate according to claim 1, wherein all part-ligands L within a cryptand K are identical.

5. The organometallic cryptate according to claim 1, wherein at least two part-ligands L are different from one another.

6. The organometallic cryptate according to claim 1, wherein the bridging unit V contains, as linking atom, an element from main group 3, 4, 5 or 6 or a 3- to 6-membered homo- or heterocycle and is neutral, singly negatively charged or singly positively charged.

7. The organometallic cryptate according to claim 1, wherein the cryptand K of the formula (4) produces a facial coordination at the metal M:

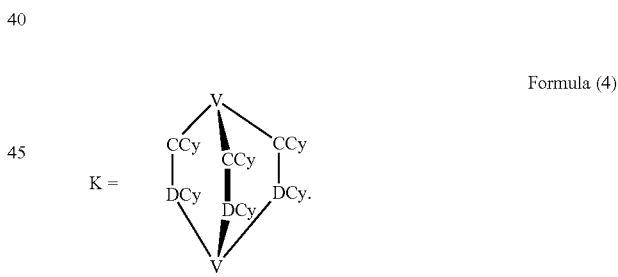

Formula (4)

8. The organometallic cryptate according to claim 1, wherein the cryptand K of the formula (5) produces a meridional coordination at the metal M:

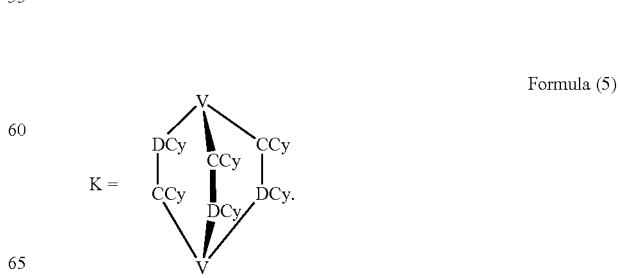

Formula (5)

9. The organometallic cryptate according to claim 1, wherein with facial coordination geometry at the metal as described by compounds (1) to (4)

Compound (1)
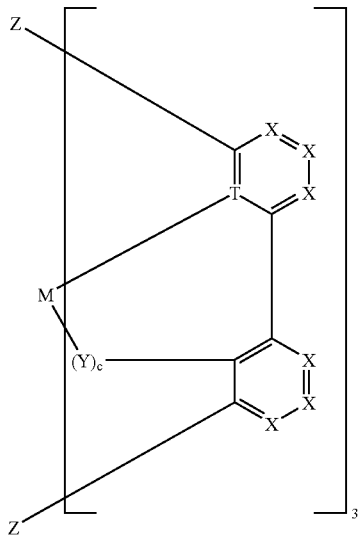

Compound (2)
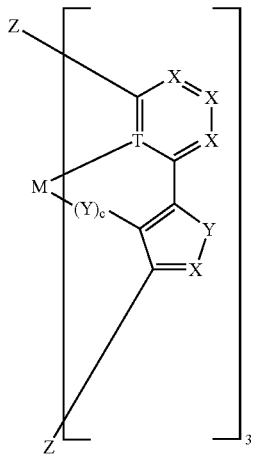

Compound (3)
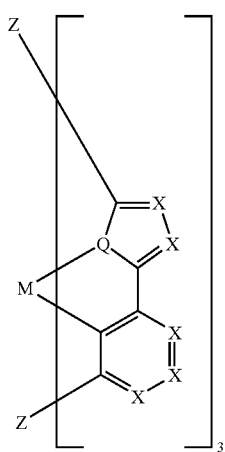

Compound (4)
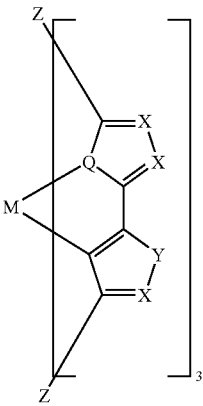

where the symbols and indices have the following meaning:
(1) M is on each occurrence, identically or differently, a main-group metal ion, a transition-metal ion or a lanthanoid ion;
(2) Q is, identically or differently on each occurrence, O, S, Se, Te or N;
(3) T is, identically or differently on each occurrence, N, P or C;
(4) X is, identically or differently on each occurrence, CR, N or P;
Y is, identically or differently on each occurrence, $NR^1$, O, S, Se, Te, SO, SeO, TeO, $SO_2$, $SeO_2$, $TeO_2$ or $R^1PO$;
Z is, identically or differently on each occurrence, B, $BR^-$, $B(CR_2)_3$, $RB(CR_2)_3^-$, $B(O)_3$, $RB(O)_3^-$, $B(CR_2CR_2)_3$, $RB(CR_2CR_2)_3^-$, $B(CR_2O)_3$, $RB(CR_2O)_3^-$, $B(OCR_2)_3$, $RB(OCR_2)_3^-$, $Al(O)_3$, $RAl(O)_3^-$, $Al(OCR_2)_3$, $RAl(OCR_2)_3^-$, CR, $CO^-$, $CNR^1_2$, $RC(CR_2)_3$, $RC(O)_3$, $RC(CR_2CR_2)_3$, $RC(CR_2O)_3$, $RC(OCR_2)_3$, $RC(SiR_2)_3$, $RC(SiR_2CR_2)_3$, $RC(CR_2SiR_2)_3$, $RC(SiR_2SiR_2)_3$, cis,cis-1,3,5-cyclohexyl, 1,3,5-$(CR_2)_3C_6H_3$, SiR, RSi$(CR_2)_3$, $RSi(O)_3$, $RSi(CR_2CR_2)_3$, $RSi(OCR_2)_3$, RSi$(CR_2O)_3$, $RSi(SiR_2)_3$, $RSi(SiR_2CR_2)_3$, $RSi(CR_2SiR_2)_3$, $RSi(SiR_2SiR_2)_3$, N, NO, $NR^+$, $N(CR_2)_3$, $RN(CR_2)_3^+$, $N(C=O)_3$, $N(CR_2CR_2)_3$, $RN(CR_2CR_2)^+$, P, PO, PS, PSe, PTe, $P(O)_3$, $P0(O)_3$, $P(OCR_2)_3$, $PO(OCR_2)_3$, $P(CR_2)_3$, $PO(CR_2)_3$, $P(CR_2CR_2)_3$, $PO(CR_2CR_2)_3$, As, AsO, AsS, AsSe, AsTe, $As(O)_3$, $AsO(O)_3$, $As(OCR_2)_3$, $AsO(OCR_2)_3$, $As(CR_2)_3$, $AsO(CR_2)_3$, $As(CR_2CR_2)_3$, $AsO(CR_2CR_2)_3$, Sb, SbO, SbS, SbSe, SbTe, $Sb(O)_3$, $SbO(O)_3$, $Sb(OCR_2)_3$, $SbO(OCR_2)_3$, $Sb(CR_2)_3$, SbO$(CR_2)_3$, $Sb(CR_2CR_2)_3$, $SbO(CR_2CR_2)_3$, Bi, BiO, BiS, BiSe, BiTe, $Bi(O)_3$, $BiO(O)_3$, $Bi(OCR_2)_3$, $BiO(OCR_2)_3$, $Bi(CR_2)_3$, $BiO(CR_2)_3$, $Bi(CR_2CR_2)_3$, $BiO(CR_2CR_2)_3$, $S^+$, $S(CR_2)_3^+$, $S(CR_2CR_2)_3^+$, $Se^+$, $Se(CR_2)_3^+$, $Se(CR_2CR_2)_3^+$, $Te^+$, $Te(CR_2)_3^+$ or $Te(CR_2CR_2)_3^+$;
R is, identically or differently on each occurrence, H, F, Cl, Br, I, OH, $NO_2$, CN, a straight-chain, branched or cyclic alkyl or alkoxy group having 1 to 20 C atoms, in which one or more non-adjacent $CH_2$ groups is optionally replaced by —$R^1C=CR^1$—, $Si(R^1)_2$, $Ge(R^1)_2$, $Sn(R^1)_2$, C=O, C=S, C=Se, C=$NR^1$, —O—, —S—, —$NR^1$— or —$CONR^1$— and in which one or more H atoms is optionally replaced by F, or an aromatic or heteroaromatic ring system having 1 to 14 C atoms, which is optionally substituted by one or more non-aromatic radicals R, where two or more substituents R, both on the same ring and also on the two different rings, together may in turn define a further mono- or polycyclic, aliphatic or aromatic and/or benzo-fused ring system;

R¹ is, identically or differently on each occurrence, H or an aliphatic or aromatic hydrocarbon radical having 1 to 20 C atoms;

c is, identically or differently on each occurrence, 0 or 1, with the proviso that c=0 if the symbol T in the corresponding part-ligand stands for N or P.

10. The organometallic cryptate according to claim 1, with meridional coordination geometry at the metal as described by compounds (5) to (8)

Compound (5)

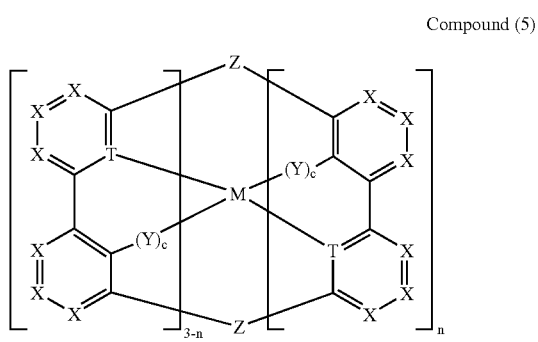

Compound (6)

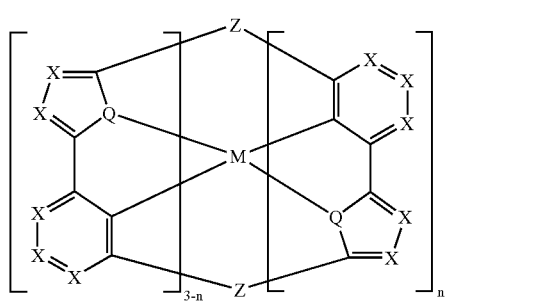

Compound (7)

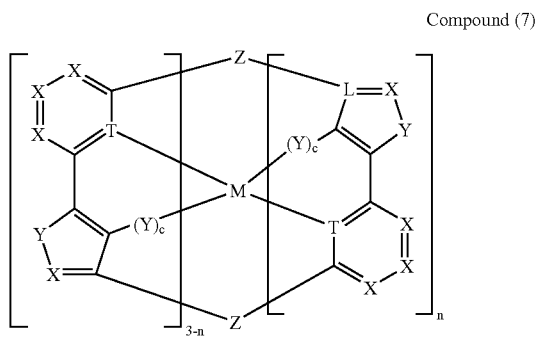

-continued

Compound (8)

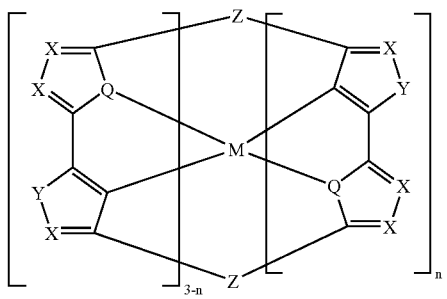

wherein

M is on each occurrence, identically or differently, a main-group metal ion, a transition-metal ion or a lanthanoid ion;

Q is, identically or differently on each occurrence, O, S, Se, Te or N;

T is, identically or differently on each occurrence, N, P or C;

X is, identically or differently on each occurrence, CR, N or P;

is, identically or differently on each occurrence, NR¹, O, S, Se, Te, SO, SeO, TeO, SO₂, SeO₂, TeO₂ or R¹PO;

Z is, identically or differently on each occurrence, B, BR⁻, B(CR₂)₃, RB(CR₂)₃⁻, B(O)₃, RB(O)₃⁻, B(CR₂CR₂)₃, RB(CR₂CR₂)₃⁻, B(CR₂O)₃, RB(CR₂O)₃⁻, B(OCR₂)₃, RB(OCR₂)₃⁻, Al(O)₃, RAl(O)₃⁻, Al(OCR₂)₃, RAl(OCR₂)₃⁻, CR, CO⁻, CNR¹₂, RC(CR₂)₃, RC(O)₃, RC(CR₂CR₂)₃, RC(CR₂O)₃, RC(OCR₂)₃, RC(SiR₂)₃, RC(SiR₂CR₂)₃, RC(CR₂SiR₂)₃, RC(SiR₂SiR₂)₃, cis, cis-1,3,5-cyclohexyl, 1,3,5-(CR₂)₃C₆H₃, SiR, RSi(CR₂)₃, RSi(O)₃, RSi(CR₂CR₂)₃, RSi(OCR₂)₃, RSi(CR₂O)₃, RSi(SiR₂)₃, RSi(SiR₂CR₂)₃, RSi(CR₂SiR₂)₃, RSi(SiR₂SiR₂)₃, N, NO, NR⁺, N(CR₂)₃, RN(CR₂)₃⁺, N(C=O)₃, N(CR₂CR₂)₃, RN(CR₂CR₂)⁺, P, PO, PS, PSe, PTe, P(O)₃, P0(O)₃, P(OCR₂)₃, PO(OCR₂)₃, P(CR₂)₃, PO(CR₂)₃, P(CR₂CR₂)₃, PO(CR₂CR₂)₃, As, AsO, AsS, AsSe, AsTe, As(O)₃, AsO(O)₃, As(OCR₂)₃, AsO(OCR₂)₃, As(CR₂)₃, AsO(CR₂)₃, As(CR₂CR₂)₃, AsO(CR₂CR₂)₃, Sb, SbO, SbS, SbSe, SbTe, Sb(O)₃, SbO(O)₃, Sb(OCR₂)₃, SbO(OCR₂)₃, Sb(CR₂)₃, SbO(CR₂)₃, Sb(CR₂CR₂)₃, SbO(CR₂CR₂)₃, Bi, BiO, BiS, BiSe, BiTe, Bi(O)₃, BiO(O)₃, Bi(OCR₂)₃, BiO(OCR₂)₃, Bi(CR₂)₃, BiO(CR₂)₃, Bi(CR₂CR₂)₃, BiO(CR₂CR₂)₃, S⁺, S(CR₂)₃⁺, S(CR₂CR₂)₃⁺, Se⁺, Se(CR₂)₃⁺, Se(CR₂CR₂)₃⁺, Te⁺, Te(CR₂)₃⁺ or Te(CR₂CR₂)₃⁺;

R is, identically or differently on each occurrence, H, F, Cl, Br, I, OH, NO₂, CN, a straight-chain, branched or cyclic alkyl or alkoxy group having 1 to 20 C atoms, in which one or more non-adjacent CH₂ groups is optionally replaced by —R¹C=CR¹—, Si(R¹)₂, Ge(R¹)₂, Sn(R¹)₂, C=O, C=S, C=Se, C=NR¹, —O—, —S—, —NR¹— or —CONR¹— and in which one or more H atoms is optionally replaced by F, or an aromatic or heteroaromatic ring system having 1 to 14 C atoms, which is optionally substituted by one or more non-aromatic radicals R, where two or more substituents R, both on the same ring and also on the two different rings, together may in turn define a further mono- or polycyclic, aliphatic or aromatic and/or benzo-fused ring system;

R[1] is, identically or differently on each occurrence, H or an aliphatic or aromatic hydrocarbon radical having 1 to 20 C atoms;

c is, identically or differently on each occurrence, 0 or 1, with the proviso that c=0 if the symbol T in the corresponding part-ligand stands for N or P;

n is equal to 1 or 2.

11. The organometallic cryptate according to claim 1, wherein the cryptate is as described by compounds (9) to (26):

Compound (9)

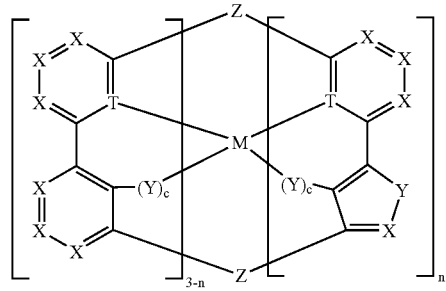

Compound (10)

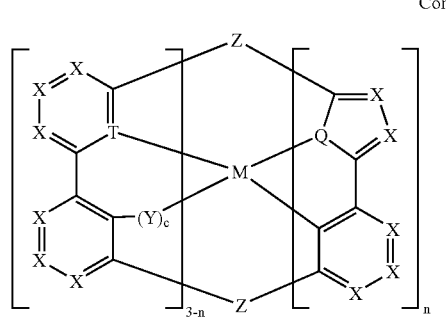

Compound (11)

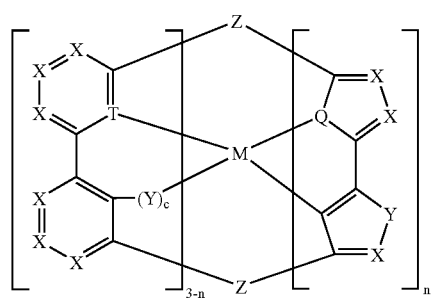

Compound (12)

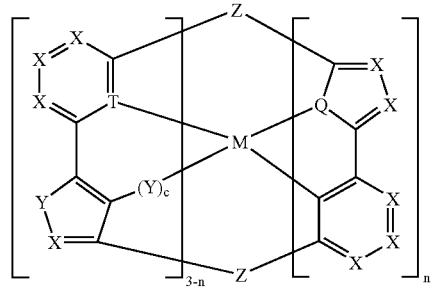

-continued

Compound (13)

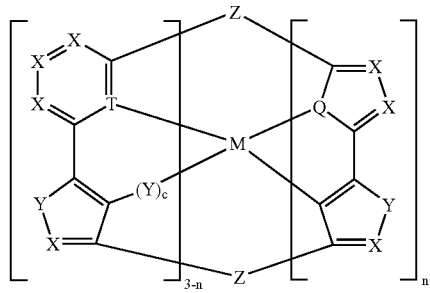

Compound (14)

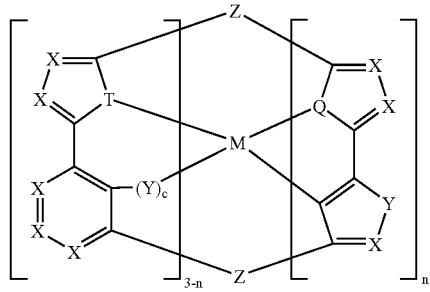

Compound (15)

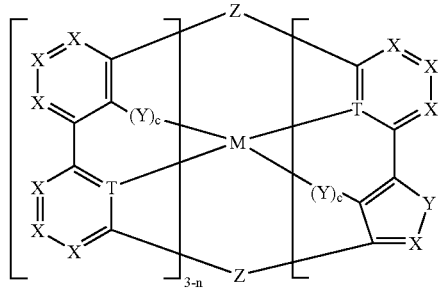

Compound (16)

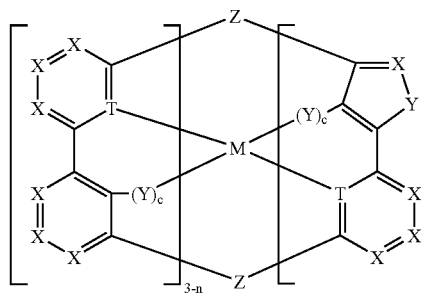

Compound (17)

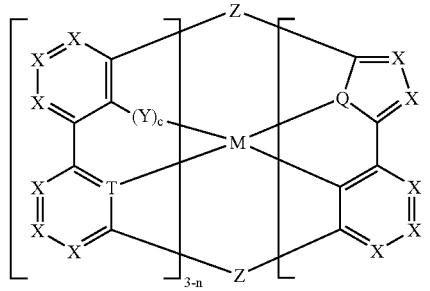

-continued

Compound (18)
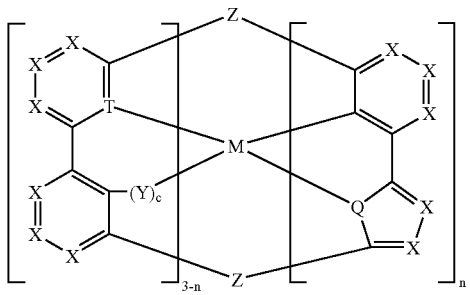

Compound (19)
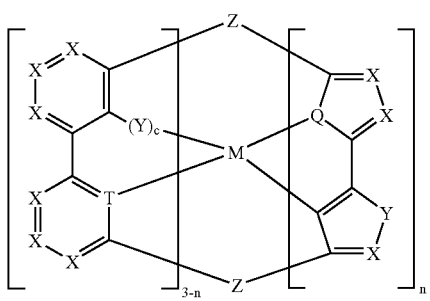

Compound (20)
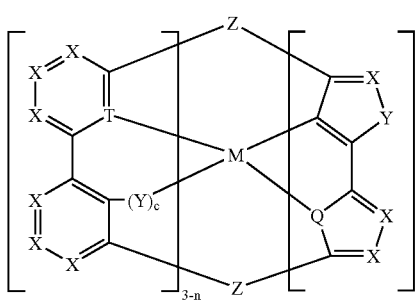

Compound (21)
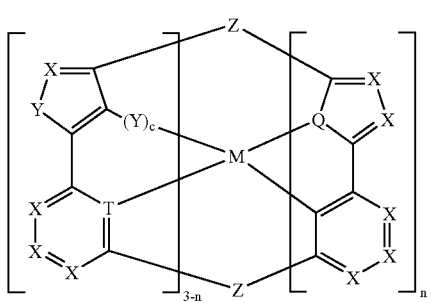

Compound (22)
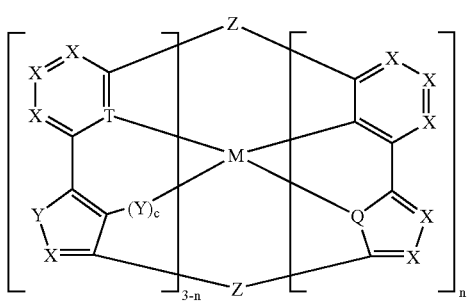

-continued

Compound (23)
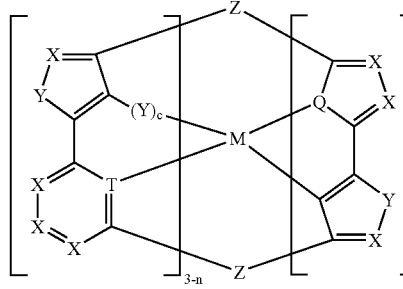

Compound (24)
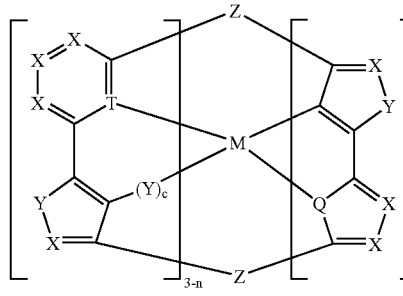

Compound (25)
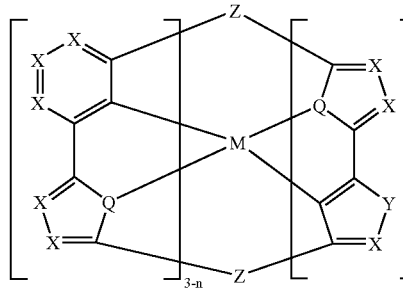

Compound (26)
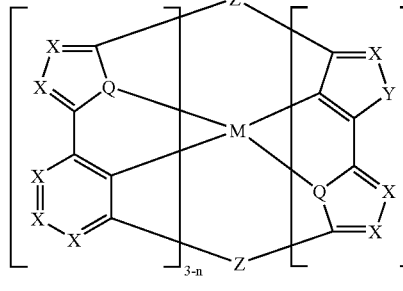

wherein

M is on each occurrence, identically or differently, a main-group metal ion, a transition-metal ion or a lanthanoid ion;

Q is, identically or differently on each occurrence, O, S, Se, Te or N;

T is, identically or differently on each occurrence, N, P or C;

X is, identically or differently on each occurrence, CR, N or P;

Y is, identically or differently on each occurrence, $NR^1$, O, S, Se, Te, SO, SeO, TeO, $SO_2$, $SeO_2$, $TeO_2$ or $R^1PO$;

Z is, identically or differently on each occurrence, B, BR⁻, B(CR₂)₃, RB(CR₂)₃⁻, B(O)₃, RB(O)₃⁻, B(CR₂CR₂)₃, RB(CR₂CR₂)₃⁻, B(CR₂O)₃, RB(CR₂O)₃⁻, B(OCR₂)₃, RB(OCR₂)₃⁻, Al(O)₃, RAl(O)₃⁻, Al(OCR₂)₃, RAl(OCR₂)₃⁻, CR, CO⁻, CNR¹₂, RC(CR₂)₃, RC(O)₃, RC(CR₂CR₂)₃, RC(CR₂O)₃, RC(OCR₂)₃, RC(SiR₂)₃, RC(SiR₂CR₂)₃, RC(CR₂SiR₂)₃, RC(SiR₂SiR₂)₃, cis, cis-1,3,5-cyclohexyl, 1,3,5-(CR₂)₃C₆H₃, SiR, RSi(CR₂)₃, RSi(O)₃, RSi(CR₂CR₂)₃, RSi(OCR₂)₃, RSi(CR₂O)₃, RSi(SiR₂)₃, RSi(SiR₂CR₂)₃, RSi(CR₂SiR₂)₃, RSi(SiR₂SiR₂)₃, N, NO, NR⁺, N(CR₂)₃, RN(CR₂)₃⁺, N(C=O)₃, N(CR₂CR₂)₃, RN(CR₂CR₂)⁺, P, PO, PS, PSe, PTe, P(O)₃, P0(O)₃, P(OCR₂)₃, PO(OCR₂)₃, P(CR₂)₃, PO(CR₂)₃, P(CR₂CR₂)₃, PO(CR₂CR₂)₃, As, AsO, AsS, AsSe, AsTe, As(O)₃, AsO(O)₃, As(OCR₂)₃, AsO(OCR₂)₃, As(CR₂)₃, AsO(CR₂)₃, As(CR₂CR₂)₃, AsO(CR₂CR₂)₃, Sb, SbO, SbS, SbSe, SbTe, Sb(O)₃, SbO(O)₃, Sb(OCR₂)₃, SbO(OCR₂)₃, Sb(CR₂)₃, SbO(CR₂)₃, Sb(CR₂CR₂)₃, SbO(CR₂CR₂)₃, Bi, BiO, BiS, BiSe, BiTe, Bi(O)₃, BiO(O)₃, Bi(OCR₂)₃, BiO(OCR₂)₃, Bi(CR₂)₃, BiO(CR₂)₃, Bi(CR₂CR₂)₃, BiO(CR₂CR₂)₃, S⁺, S(CR₂)₃⁺, S(CR₂CR₂)₃⁺, Se⁺, Se(CR₂)₃⁺, Se(CR₂CR₂)₃⁺, Te⁺, Te(CR₂)₃⁺ or Te(CR₂CR₂)₃⁺;

R is, identically or differently on each occurrence, H, F, Cl, Br, I, OH, NO₂, CN, a straight-chain, branched or cyclic alkyl or alkoxy group having 1 to 20 C atoms, in which one or more non-adjacent CH₂ groups is optionally replaced by —R¹C=CR¹—, Si(R¹)₂, Ge(R¹)₂, Sn(R¹)₂, C=O, C=S, C=Se, C=NR¹, —O—, —S—, —NR¹— or —CONR¹— and in which one or more H atoms is optionally replaced by F, or an aromatic or heteroaromatic ring system having 1 to 14 C atoms, which is optionally substituted by one or more non-aromatic radicals R, where two or more substituents R, both on the same ring and also on the two different rings, together may in turn define a further mono- or polycyclic, aliphatic or aromatic and/or benzo-fused ring system;

R¹ is, identically or differently on each occurrence, H or an aliphatic or aromatic hydrocarbon radical having 1 to 20 C atoms;

c is, identically or differently on each occurrence, 0 or 1, with the proviso that c=0 if the symbol T in the corresponding part-ligand stands for N or P; and n is equal to 1 or 2.

12. The organometallic cryptate according to claim 9, wherein M on each occurrence, identically or differently, represents a transition-metal ion.

13. The organometallic cryptate according to claim 9, wherein Q on each occurrence, identically or differently, represents O, S or Se.

14. The organometallic cryptate according to claim 9, wherein T on each occurrence, identically or differently, represents N or P.

15. The organometallic cryptate according to claim 9, wherein X on each occurrence, identically or differently, represents CR or N.

16. The organometallic cryptate according claim 9, wherein Z on each occurrence, identically or differently, represents B, BR⁻, B(CR₂)₃, RB(CR₂)₃⁻, B(O)₃, RB(O)₃⁻, B(OCR₂)₃, RB(OCR₂)₃⁻, Al(O)₃, RAl(O)₃⁻, Al(OCR₂)₃, RAl(OCR₂)₃⁻, CR, CNR¹₂, RC(CR₂)₃, RC(O)₃, RC(CR₂CR₂)₃, RC(CR₂O)₃, RC(OCR₂)₃, SiR, RSi(CR₂)₃, RSi(O)₃, RSi(CR₂CR₂)₃, RSi(OCR₂)₃, RSi(CR₂O)₃, N, NO, NR⁺, N(CR₂)₃, RN(CR₂)₃⁺, N(C=O)₃, N(CR₂CR₂)₃, RN(CR₂CR₂)⁺, P, PO, P(O)₃, P0(O)₃, P(OCR₂)₃, PO(OCR₂)₃, S⁺, S(CR₂)₃⁺ or S(CR₂CR₂)₃⁺.

17. The organometallic cryptate according to claim 9, wherein Y on each occurrence, identically or differently, represents O, S or NR¹.

18. The organometallic cryptate according to claim 9, wherein the index c on each occurrence is equal to 0.

19. Conjugated, partially conjugated or non-conjugated polymer or dendrimer containing one or more organometallic cryptates according to claim 9, where one or more of the substituents R represent a bond to the polymer or dendrimer.

20. The polymer according to claim 19, wherein the polymer is soluble polyfluorene, polyspirobifluorene, poly-para-phenylene, polycarbazole, polydihydro-phenanthrene, polyphenanthrene, polyvinylcarbazole, polythiophene, silane-containing polymer or copolymer comprising a plurality of these polymers.

21. A cryptand which comprises a compound selected from a compound of formulas (27) to (52)

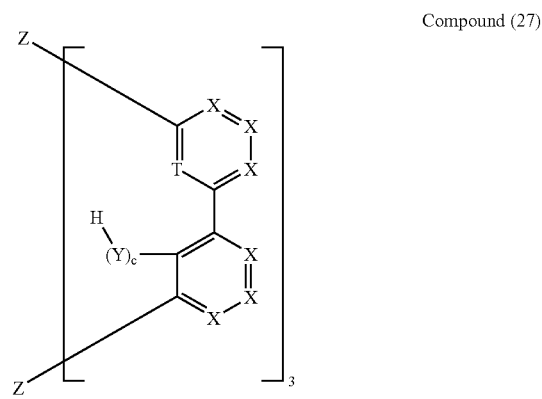

Compound (27)

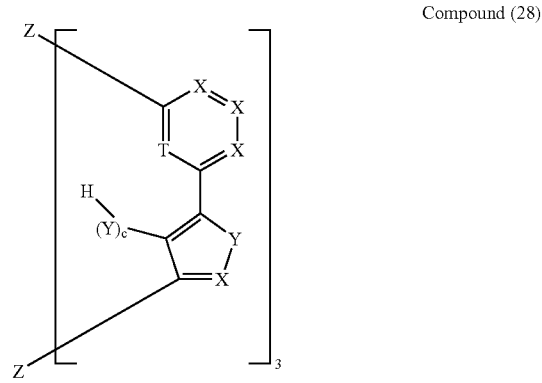

Compound (28)

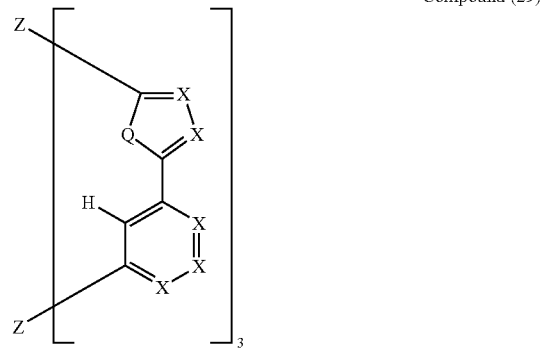

Compound (29)

-continued
Compound (30)
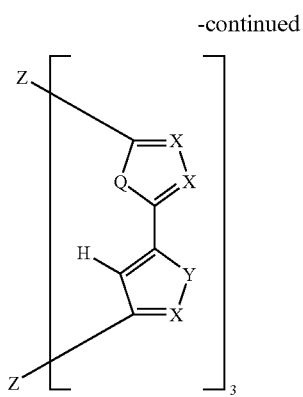
Compound (31)
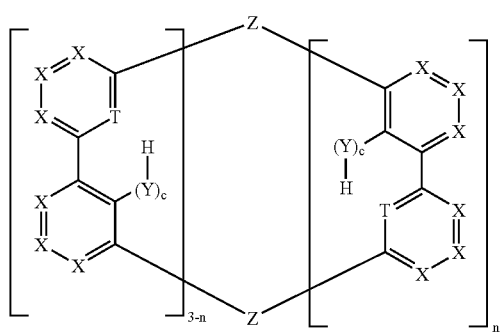
Compound (32)
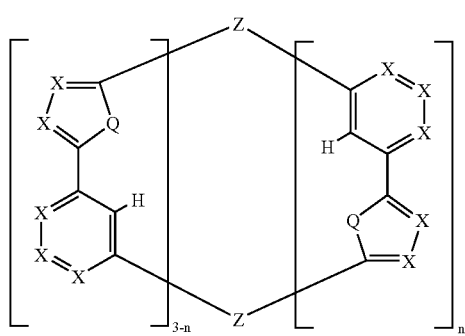
Compound (33)
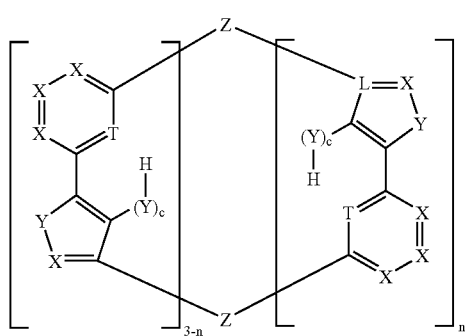
Compound (34)
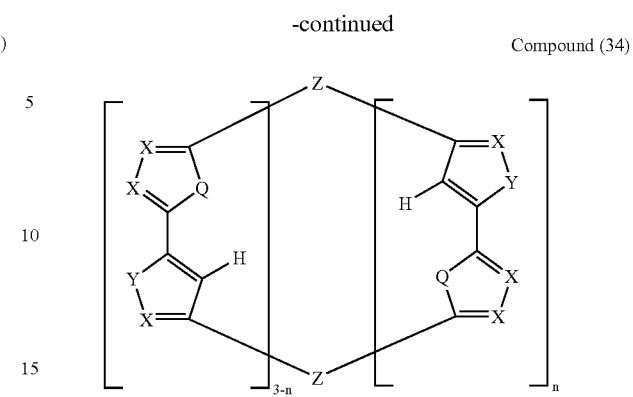
Compound (35)
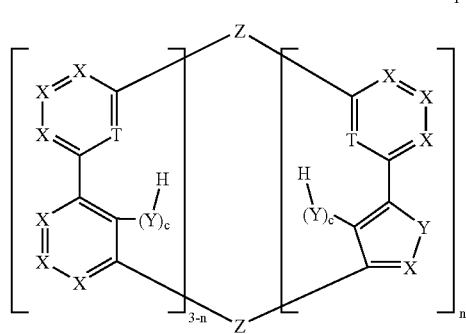
Compound (36)
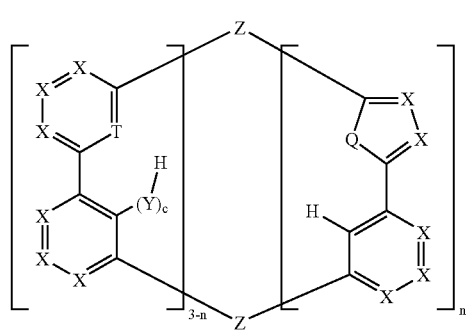
Compound (37)
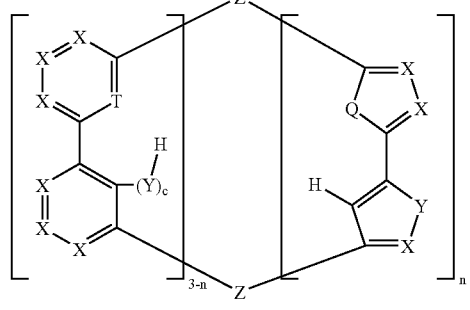

Compound (38)
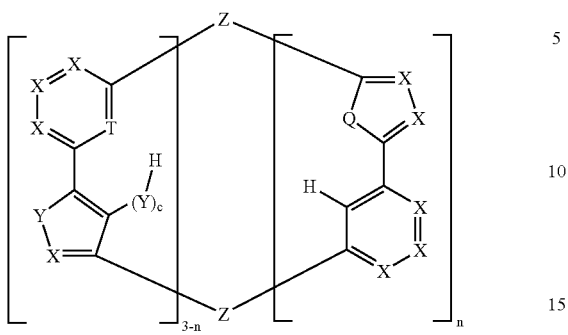
Compound (42)
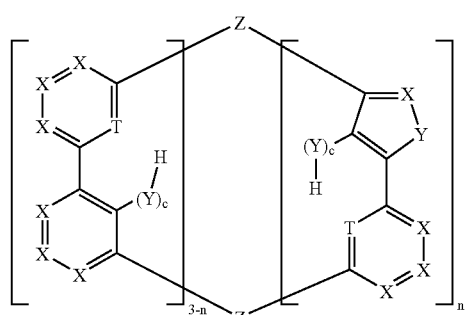
Compound (39)
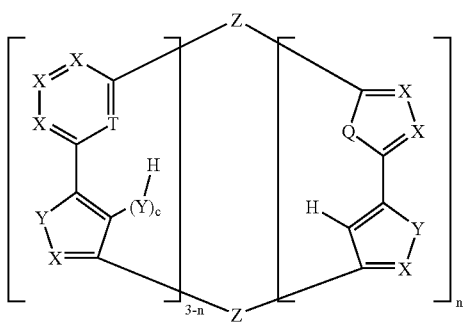
Compound (43)
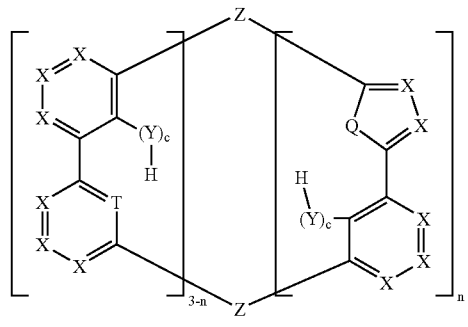
Compound (40)
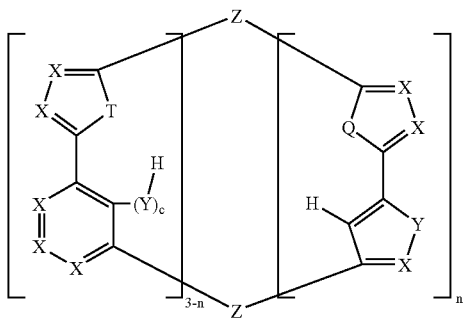
Compound (44)
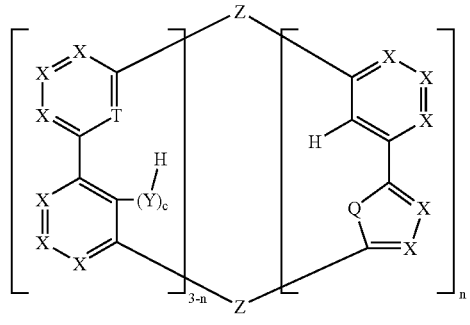
Compound (41)
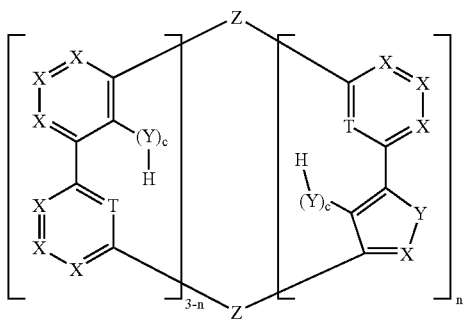
Compound (45)
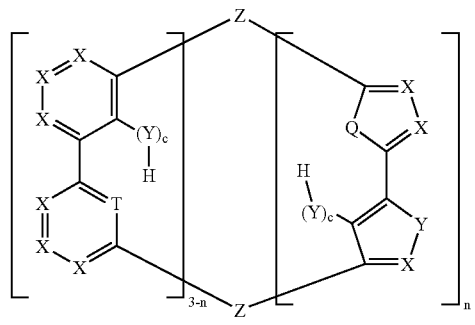

-continued

Compound (46)
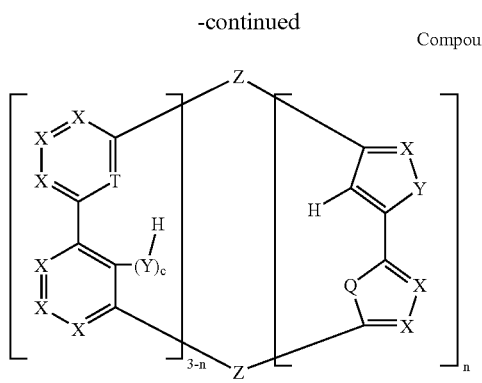

Compound (47)
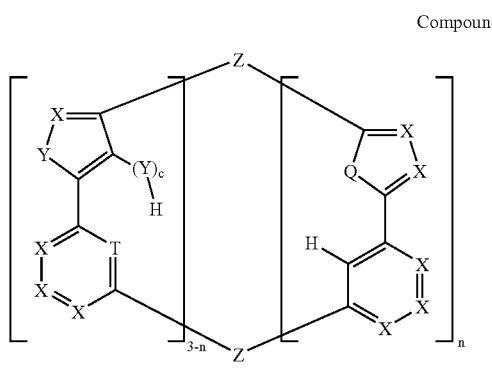

Compound (48)
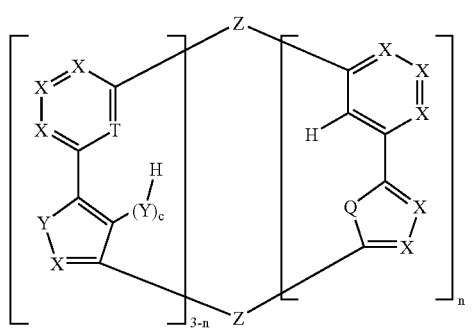

Compound (49)
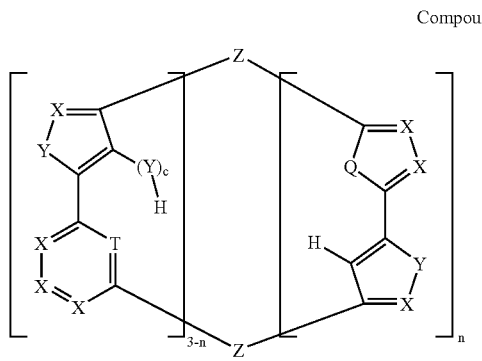

-continued

Compound (50)
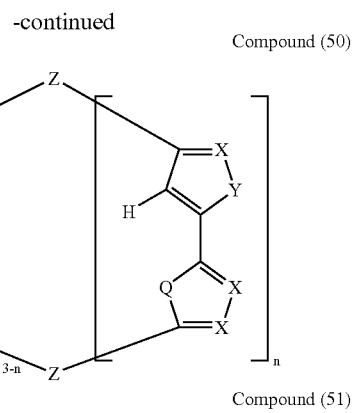

Compound (51)
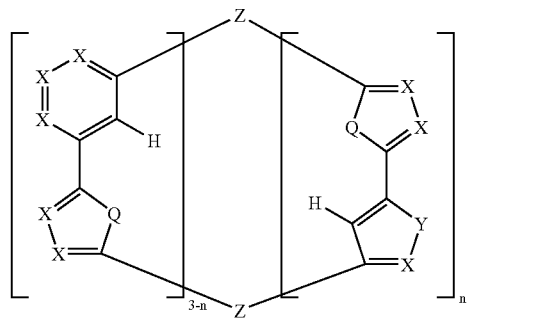

Compound (52)
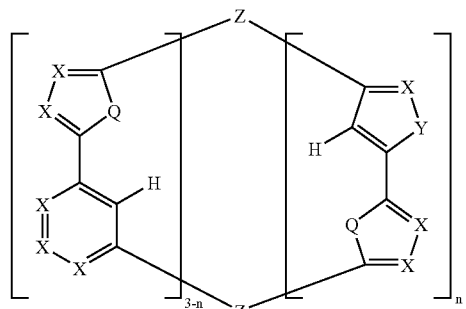

wherein

M is on each occurrence, identically or differently, a main-group metal ion, a transition-metal ion or a lanthanoid ion;

Q is, identically or differently on each occurrence, O, S, Se, Te or N;

T is, identically or differently on each occurrence, N, P or C;

X is, identically or differently on each occurrence, CR, N or P;

Y is, identically or differently on each occurrence, $NR^1$, O, S, Se, Te, SO, SeO, TeO, $SO_2$, $SeO_2$, $TeO_2$ or $R^1PO$;

Z is, identically or differently on each occurrence, B, $BR^-$, $B(CR_2)_3$, $RB(CR_2)_3^-$, $B(O)_3$, $RB(O)_3^-$, $B(CR_2CR_2)_3$, $RB(CR_2CR_2)_3^-$, $B(CR_2O)_3$, $RB(CR_2O)_3^-$, $B(OCR_2)_3$, $RB(OCR_2)_3^-$, $Al(O)_3$, $RAl(O)_3^-$, $Al(OCR_2)_3$, $RAl(OCR_2)_3^-$, CR, $CO^-$, $CNR^1_2$, $RC(CR_2)_3$, $RC(O)_3$, $RC(CR_2CR_2)_3$, $RC(CR_2O)_3$, $RC(OCR_2)_3$, $RC(SiR_2)_3$, $RC(SiR_2CR_2)_3$, $RC(CR_2SiR_2)_3$, $RC(SiR_2SiR_2)_3$, cis, cis-1,3,5-cyclohexyl, 1,3,5-$(CR_2)_3C_6H_3$, SiR, RSi $(CR_2)_3$, $RSi(O)_3$, $RSi(CR_2CR_2)_3$, $RSi(OCR_2)_3$, $RSi(CR_2O)_3$, $RSi(SiR_2)_3$, $RSi(SiR_2CR_2)_3$, $RSi(CR_2SiR_2)_3$, $RSi(SiR_2SiR_2)_3$, N, NO, $NR^+$, $N(CR_2)_3$, $RN(CR_2)_3^+$, N(C=O)₃, N(CR₂CR₂)₃, RN(CR₂CR₂)⁺, P, PO, PS, PSe, PTe, P(O)₃, P0(O)₃, P(OCR₂)₃, PO(OCR₂)₃, P(CR₂)₃, PO(CR₂)₃, P(CR₂CR₂)₃, PO(CR₂CR₂)₃, As, AsO, AsS, AsSe, AsTe, As(O)₃, AsO(O)₃, As(OCR₂)₃, AsO(OCR₂)₃, As(CR₂)₃, AsO(CR₂)₃, As(CR₂CR₂)₃, AsO(CR₂CR₂)₃, Sb, SbO, SbS, SbSe, SbTe, Sb(O)₃, SbO(O)₃, Sb(OCR₂)₃, SbO(OCR₂)₃, Sb(CR₂)₃, SbO(CR₂)₃, Sb(CR₂CR₂)₃, SbO(CR₂CR₂)₃, Bi, BiO, BiS, BiSe, BiTe, Bi(O)₃, BiO(O)₃, Bi(OCR₂)₃, BiO(OCR₂)₃, Bi(CR₂)₃, BiO(CR₂)₃, Bi(CR₂CR₂)₃, BiO(CR₂CR₂)₃, S⁺, S(CR₂)₃⁺, S(CR₂CR₂)₃⁺, Se⁺, Se(CR₂)₃⁺, Se(CR₂CR₂)₃⁺, Te⁺, Te(CR₂)₃⁺ or Te(CR₂CR₂)₃⁺;

R is, identically or differently on each occurrence, H, F, Cl, Br, I, OH, NO₂, CN, a straight-chain, branched or cyclic alkyl or alkoxy group having 1 to 20 C atoms, in which one or more non-adjacent CH₂ groups is optionally replaced by —R¹C=CR¹—, Si(R¹)₂, Ge(R¹)₂, Sn(R¹)₂, C=O, C=S, C=Se, C=NR¹, —O—, —S—, —NR¹— or —CONR¹— and in which one or more H atoms is optionally replaced by F, or an aromatic or heteroaromatic ring system having 1 to 14 C atoms, which is optionally substituted by one or more non-aromatic radicals R, where two or more substituents R, both on the same ring and also on the two different rings, together may in turn define a further mono- or polycyclic, aliphatic or aromatic and/or benzo-fused ring system;

R¹ is, identically or differently on each occurrence, H or an aliphatic or aromatic hydrocarbon radical having 1 to 20 C atoms;

c is, identically or differently on each occurrence, 0 or 1, with the proviso that c=0 if the symbol T in the corresponding part-ligand stands for N or P; and n is equal to 1 or 2.

22. A process for the preparation of organometallic cryptate which comprises reacting the cryptand according to claim 21 or precursors of these cryptands with metal alkoxides as described by compound (53), with metal ketoketonates as described by compound (54) or metal halides as described by compound (55)

M(OR¹)ₚ     Compound (53)

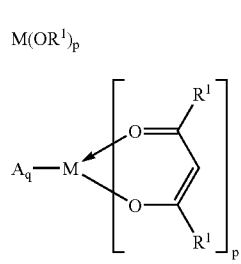

Compound (54)

MHalₚ     Compound (55)

where the following applies to the symbols and indices:

M is on each occurrence, identically or differently, a main-group metal ion, a transition-metal ion or a lanthanoid ion;

Hal is on each occurrence, identically or differently, F, Cl, Br or I;

A is on each occurrence, identically or differently, a neutral or monoanionic, monodentate or bidentate ligand;

p is on each occurrence, identically or differently, 1, 2, 3, 4 or 5, where p in compounds (53) and (55) indicates the valency of the metal M;

q is on each occurrence, identically or differently, 0, 1, 2, 3 or 4; and

R¹ is, identically or differently on each occurrence, H or an aliphatic or aromatic hydrocarbon radical having 1 to 20 C atoms;

compound (54) is optionally charged and optionally contains a counterion.

23. The process according to claim 22, wherein a polypodal precursor of the cryptand is employed in the complexing step, and the second bridging unit V or Z is introduced in a second synthesis step:

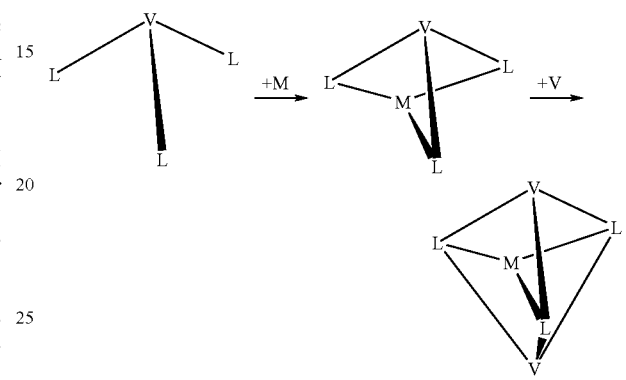

or in that a simple precursor of the cryptand is employed, and both bridging units V and Z are formed:

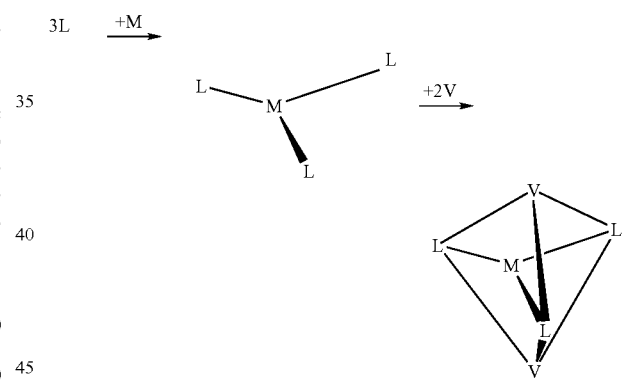

or in that a macrocyclic precursor of the cryptand is employed, and the third part-ligand L is introduced and linked to the bridging units V or Z:

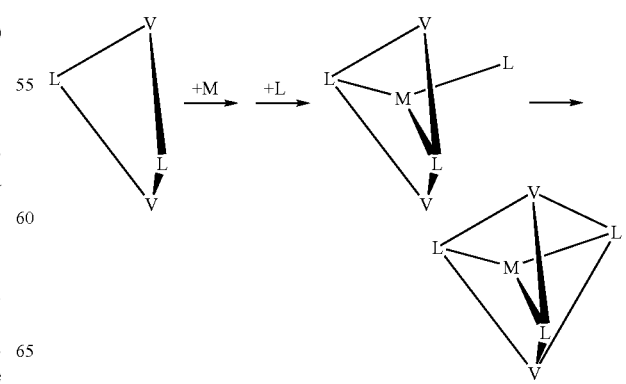

24. An organic electronic component comprising one or more cryptates.

25. An organic electronic component comprising one or more of the cryptates according to claim 1.

26. The organic electronic component claim 25 wherein the component is organic light-emitting diode (OLED), organic integrated circuit (O-IC), organic field-effect transistor (OFET), organic thin-film transistor (OTFT), organic solar cell (O-SC), organic optical detector or organic laser diode (O-laser).

* * * * *